(12) United States Patent
Hadj Henni et al.

(10) Patent No.: US 10,288,541 B2
(45) Date of Patent: May 14, 2019

(54) SYSTEM AND METHOD FOR MEASUREMENTS OF VISCOELASTIC PARAMETERS IN SOFT MATERIALS

(71) Applicant: RHEOLUTION INC., Montréal (CA)

(72) Inventors: Anis Redha Hadj Henni, Montréal (CA); Cédric René Schmitt, Montréal (CA)

(73) Assignee: RHEOLUTION INC., Montreal (CA)

( * ) Notice: Subject to any disclaimer, the term of this patent is extended or adjusted under 35 U.S.C. 154(b) by 304 days.

(21) Appl. No.: 14/915,020

(22) PCT Filed: Aug. 27, 2014

(86) PCT No.: PCT/CA2014/050820
§ 371 (c)(1),
(2) Date: Feb. 26, 2016

(87) PCT Pub. No.: WO2015/027336
PCT Pub. Date: Mar. 5, 2015

(65) Prior Publication Data
US 2016/0274015 A1 Sep. 22, 2016

Related U.S. Application Data

(60) Provisional application No. 61/870,426, filed on Aug. 27, 2013, provisional application No. 61/870,353, filed on Aug. 27, 2013.

(51) Int. Cl.
*G01N 3/32* (2006.01)
*G01N 11/10* (2006.01)
(Continued)

(52) U.S. Cl.
CPC .............. *G01N 11/16* (2013.01); *G01N 3/32* (2013.01); *G01N 3/34* (2013.01); *G01N 11/10* (2013.01);
(Continued)

(58) Field of Classification Search
CPC ............. G01N 3/38; G01N 2203/0016; G01N 2203/0226; G01N 2203/0094; G01N 3/08;
(Continued)

(56) References Cited

U.S. PATENT DOCUMENTS 3,901,074 A * 8/1975 Douglas ................. G01N 3/068
 73/579
6,205,862 B1 * 3/2001 Nakamura ............... G01N 3/00
 73/796
(Continued)

FOREIGN PATENT DOCUMENTS

EP 0921388 6/1999

OTHER PUBLICATIONS

Ceccaldi et al.; New Instrument for Real-Time Monitoring of Viscoelasticity of Soft Biomaterials and Engineered Tissues; Abstract #694; © 2014 Society for Biomaterials.
(Continued)

*Primary Examiner* — Lisa M Caputo
*Assistant Examiner* — Brandi N Hopkins
(74) *Attorney, Agent, or Firm* — Price Heneveld LLP

(57) ABSTRACT

There is provided a system and method for the measurements of viscoelastic properties of a soft sample in which the system incorporates a sample holder that has a membrane with a flexural rigidity that is less than the flexural rigidity of the main body and allowing vibration of the membrane-sample vibration unit in response to a vibration excitation to create resonance vibration modes that are detected to derive the viscoelastic properties.

20 Claims, 35 Drawing Sheets

(51) Int. Cl.
  *G01N 11/00* (2006.01)
  *G01N 11/16* (2006.01)
  *G01N 3/34* (2006.01)

(52) U.S. Cl.
  CPC ............ *G01N 2011/0026* (2013.01); *G01N 2203/0005* (2013.01); *G01N 2203/0019* (2013.01); *G01N 2203/0023* (2013.01); *G01N 2203/0094* (2013.01)

(58) Field of Classification Search
  CPC ... G01N 2203/0003; G01N 2203/0017; G01N 2203/005; G01N 2203/0222; G01N 2203/0007; G01N 2203/0037; G01N 2203/0208; G01N 11/16; G01N 2203/0005; G01N 3/34; G01N 3/32; G01N 2203/0019; G01N 11/10; G01N 2203/0023; G01N 2011/0026; G01N 3/068; G01N 2203/0051
  See application file for complete search history.

(56) References Cited

U.S. PATENT DOCUMENTS 6,386,045 B1 * 5/2002 Nakamura ............... G01N 3/32
                                                      73/760
2013/0174666 A1  7/2013  Henni et al.

OTHER PUBLICATIONS

Canadian Intellectual Property Office; International Search Report; dated Nov. 25, 2014.

http://www.rheolution.com/elastosens-bio2.html © 2016 Rheolution Inc.

http://www.rheolution.com/elastosens-x3.html © 2016 Rheolution Inc.

* cited by examiner

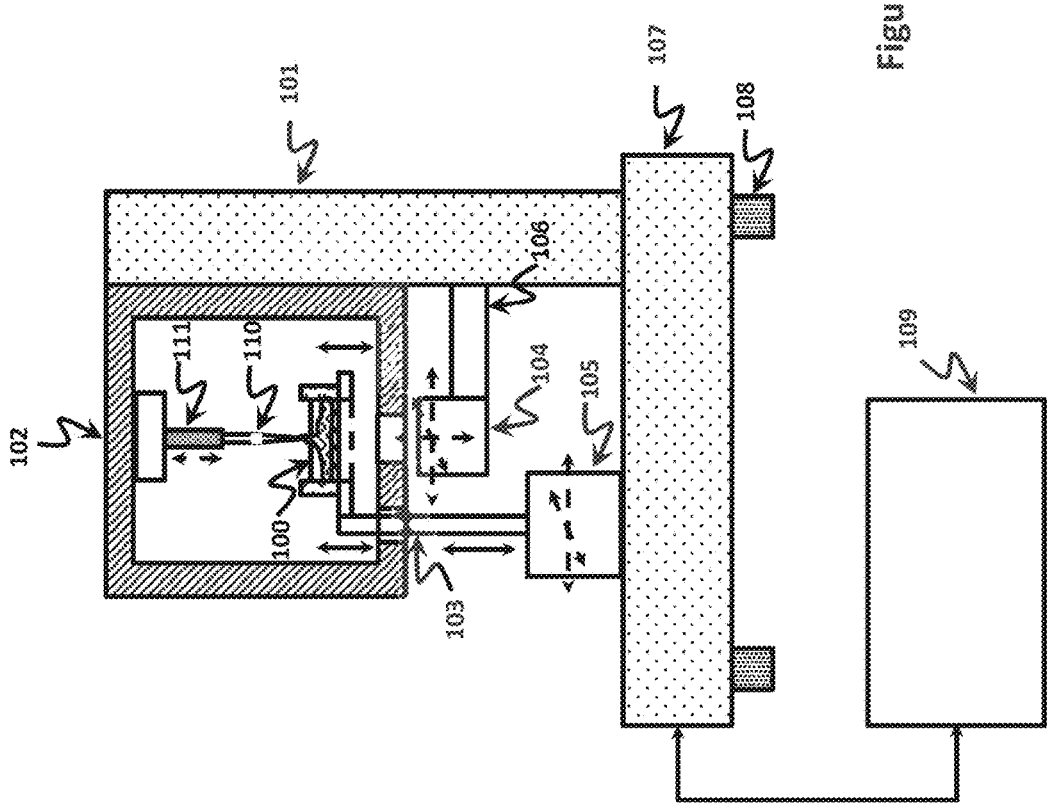

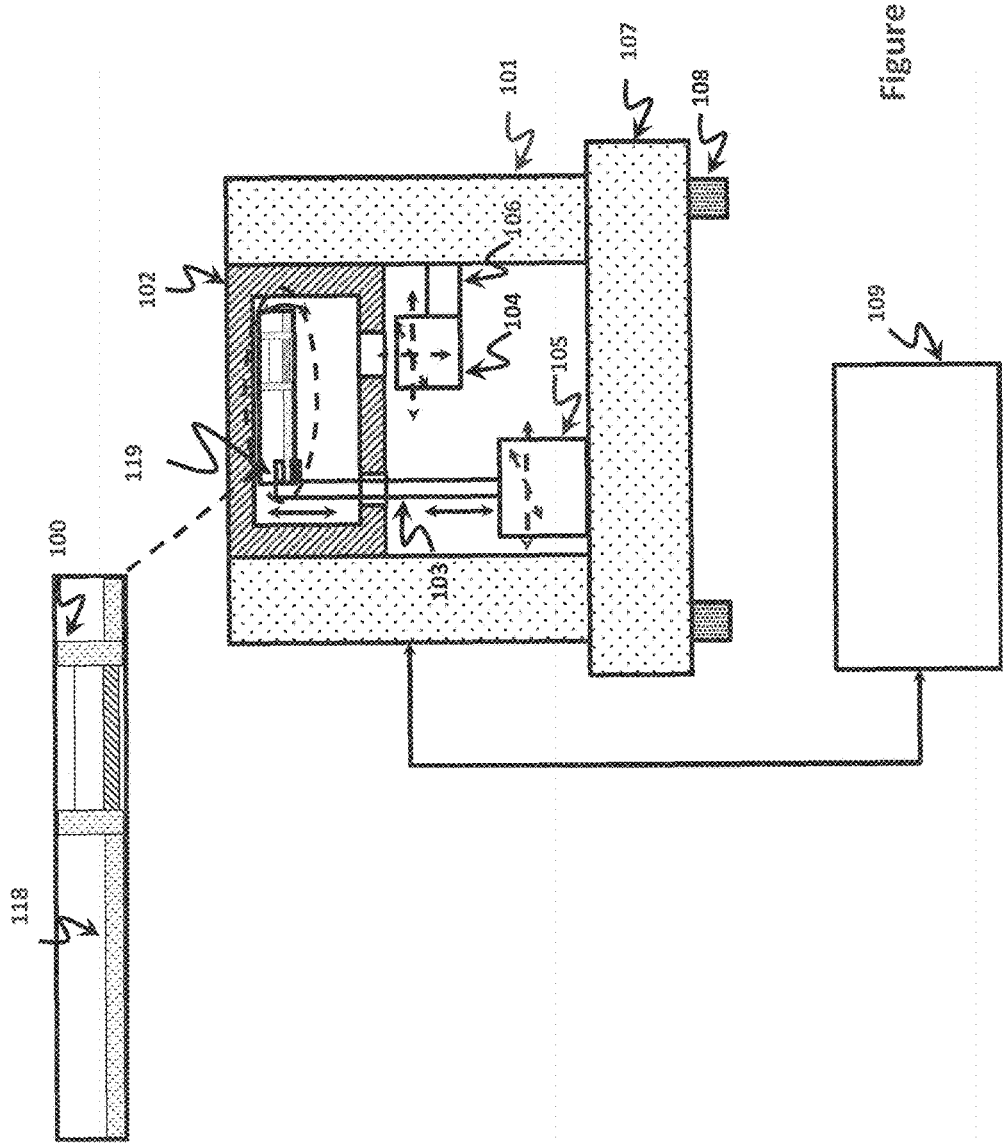

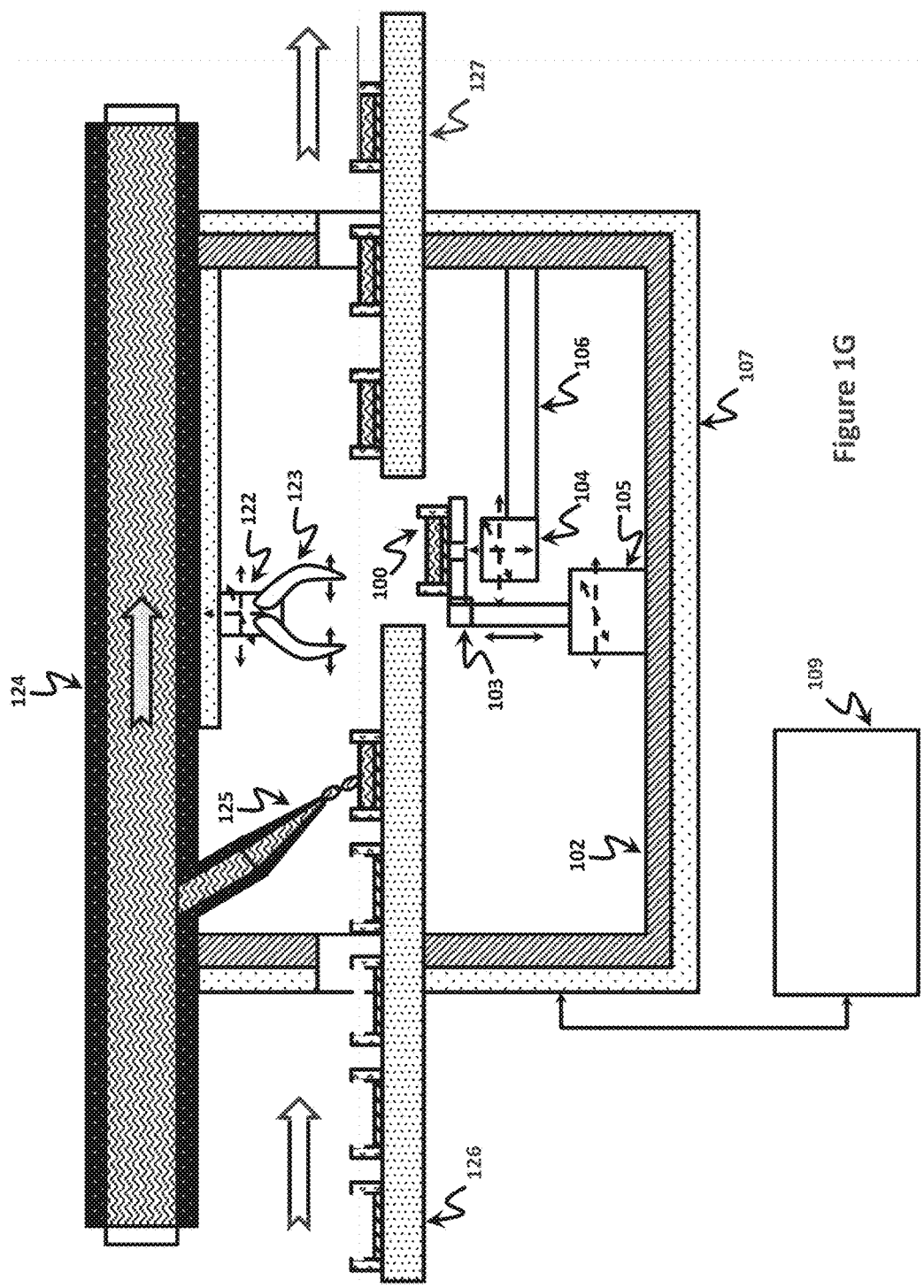

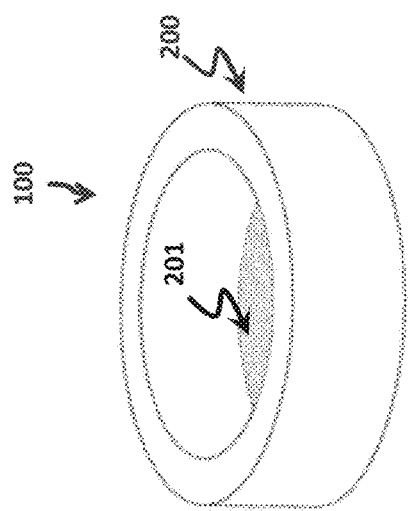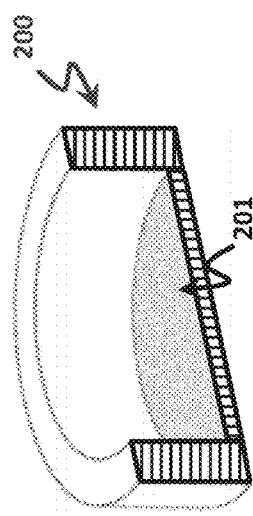
Figure 2A
Figure 2B

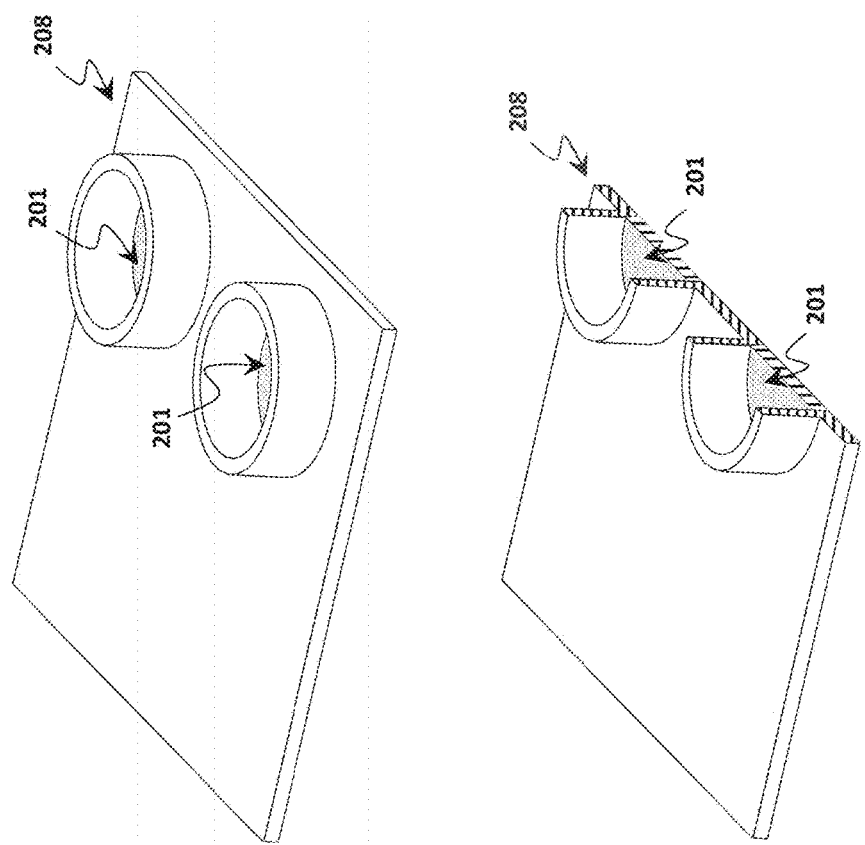

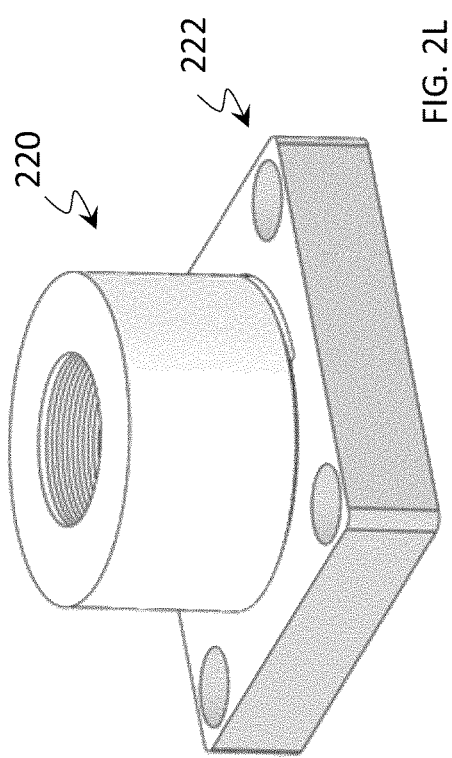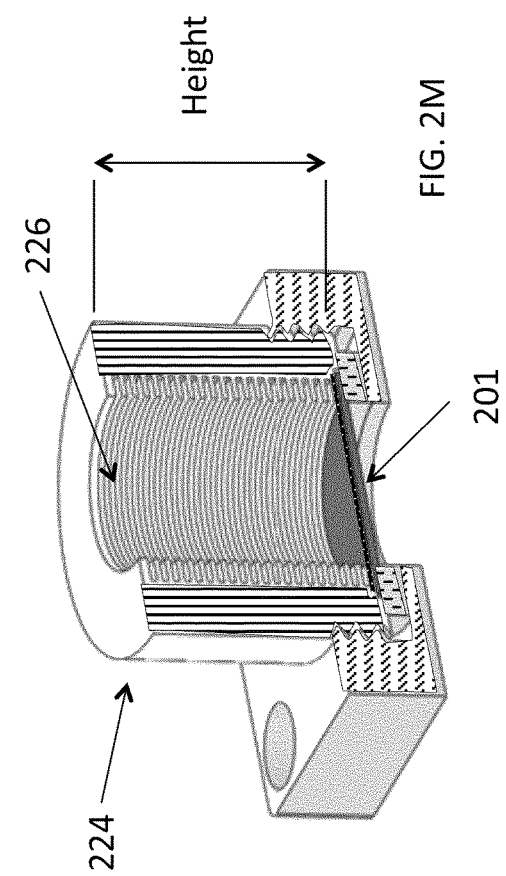

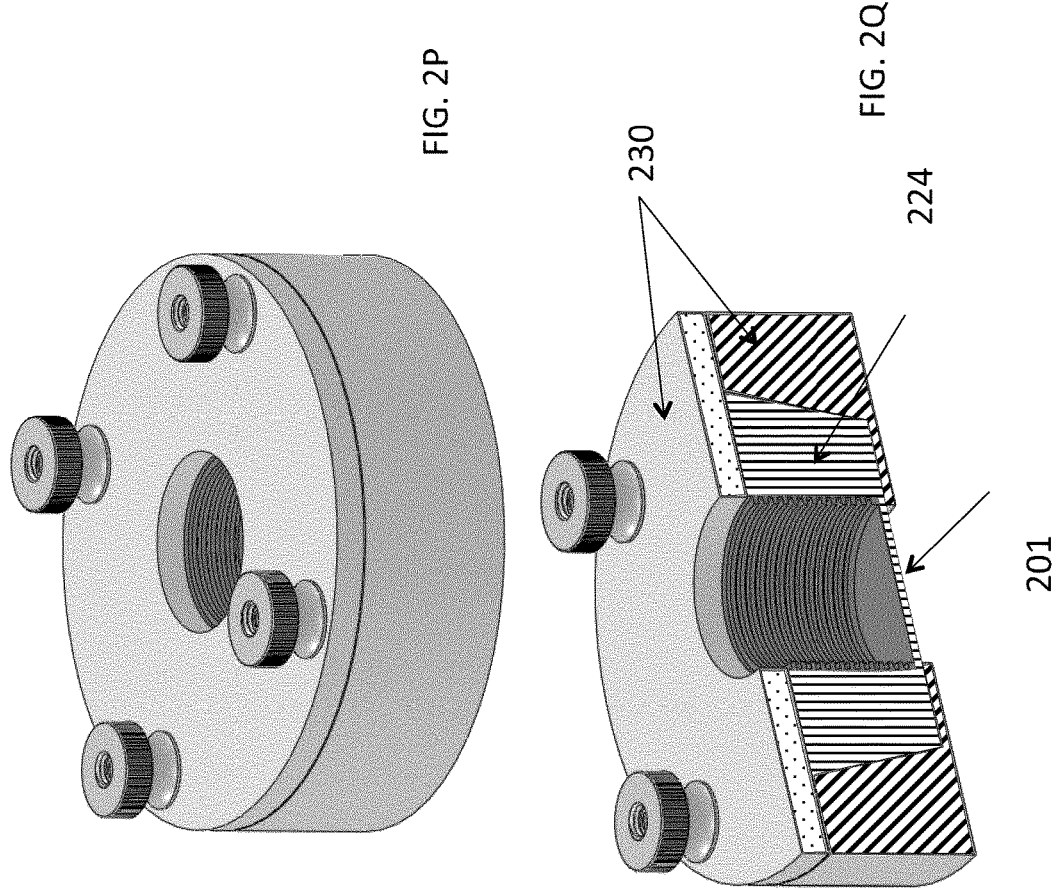

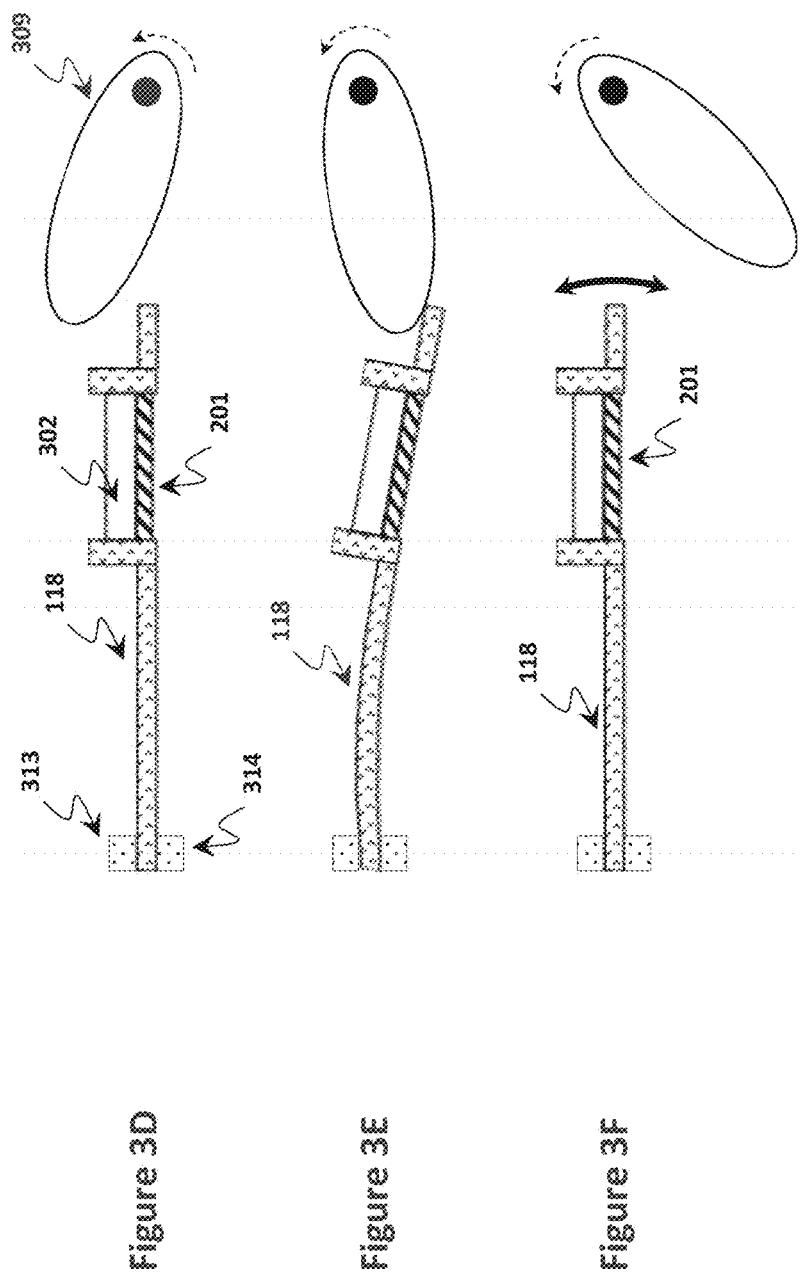

SYSTEM AND METHOD FOR MEASUREMENTS OF VISCOELASTIC PARAMETERS IN SOFT MATERIALS

TECHNICAL FIELD

This invention relates generally to measurements of viscoelastic properties of materials. More specifically, this invention relates to systems and methods for measuring viscoelastic properties of soft materials.

BACKGROUND

The characterization of the stiffness of materials is of importance in many fields. In particular, stiffness measurements can provide information on the physical states of materials that can be utilized to design objects, infrastructures, vehicles, etc. . . . . Stiffness measurements refer to a broad range of physical parameters measurements that include rheological properties, viscoelastic properties, shear stress and the like. Each of these subfields is governed by theoretical models that are used to extract specific values broadly related to the degree of rigidity of materials. The methods used to measure these properties are generally well known.

Certain types of soft materials are important economically and for public health and measurements of viscoelastic properties of these products provide valuable information. Two categories of such products are food products and biological materials.

Blood is one example of biological materials that is amenable to viscoelastic properties measurements. The mechanical properties of blood clots during the coagulation kinetic are related to the physiological state of the blood. There is an interest in characterizing blood coagulation in surgery to evaluate the coagulability of blood and prevent patient bleeding. In anesthesiology, the coagulation kinetic of blood is used to plan medication. The blood coagulation kinetic is also used as a point of care, emergency and laboratory tool to help diagnose blood disorders, which are related to many diseases, and to plan medication, to test anti-coagulant and procoagulant medicines.

The coagulation of blood is a complex polymerization process during which the blood changes from liquid to solid (coagulated) state. During clotting, the mechanical properties of blood change significantly over time due to the formation of a dense fibrin network in which are entrapped the red blood cells and other blood constituents. Since the change in mechanical properties is directly related to the composition and physiological state of the blood, several technologies and methods have been proposed to mechanically characterize blood coagulation kinetic. We can cite, among these technologies, the thromboelastography and the thromboelastometry. These techniques are inspired from rheometry. The blood sample is mixed with a coagulation reagent and poured in a cylindrical cup. A pin is inserted into the blood and the clot is formed between the pin and the cup. Depending on the technology, the cup or the pin oscillates at given frequency and amplitude to deform the clot. A probe measures the clot deformability under the external stress. The displacement of the moving part is recorded and qualitative data, related to the stiffness of the clot, are displayed as function of time. Thromboelastography and thromboelastometry are well established technologies that proved that mechanical characterization of blood during clotting provides relevant clinical information. However, these technologies are qualitative since they do not measure directly the elastic properties of the clot. Indeed, these technologies measure and display data that are indirectly related to the stiffness of the clot (in term of displacement, for example). Furthermore these techniques have relatively poor sensitivity and reproducibility.

The development of biomaterials for tissue regeneration and in vitro cell culture techniques are reshaping the future of medicine. The development of synthetic and biological biomaterials for medical uses implies rigorous investigations in: biology, physiology, pharmacology and mechanics. This latter is a key element in the success of in vitro and in vivo cellular culture, tissue regeneration and tissue engineering. Mechanical properties play an important role in the physiological functionality of tissues. For example, a vessel replacement tissue has to present precise viscoelastic properties in order to mimic (or reproduce) natural vessel tissue deformability, which critically impacts the regulation of the blood volume and pressure. Similarly, skin tissues engineering aims to produce flexible tissues in order to mimic skin flexibility and elasticity. It is then necessary to measure the viscoelastic properties of biomaterials in order to control their mechanical properties.

Among the technologies used to characterize in vitro biomaterials and cell cultures we can cite: rheometry, extensiometry and compression, indentation and atomic force microscopy (AFM). Rheometry and tension/compression present the disadvantage of destroying the sample, so it is very difficult to reuse the samples for multiple measurements over time. This important limitation in tissue engineering is due to the cost of the raw material, and the fact that cell growth can differ from one sample to another. Indentation and AFM do not damage the samples however, since measurements are very localized (micro and nano-scale for AFM), the viscoelastic characteristics are not representative of the bulk biomaterial properties. Furthermore it is difficult or impossible to use these techniques while keeping the sample sterile.

The food industry also benefits from measurements of viscoelastic properties in particular products related to milk and milk derivatives. Milk coagulates, under the action of special enzymes and coagulant agents, to form a soft gel. The coagulation and fermentation of animal milk is an important step in the preparation of food products like cheese, yogurt and other milk based soft solid products. The coagulation is also a key step in the preparation of tofu from soymilk. Coagulation of animal and vegetal milks has been extensively studied in food industry in order to formulate products, to design and set industrial production process and to control the quality of products. One of the challenges is to standardize the formation of gels. In the cheese industry, for example, it is critical to precisely select the cutting time in order to obtain a final product with the desired specifications (e.g. humidity) and to optimize the yield. The cutting time is directly related to the viscoelastic properties of the curd (the gel formed by coagulated milk). Depending on the variety of cheese, the suitable cutting time is the moment when the curd presents certain elasticity during the gelation kinetic. Cutting time has an important impact on the productivity in the cheese industry (amount of cheese per liter of milk). The preparation of yogurt also involves a viscoelastic change during the gelation kinetic (i.e. the fermentation of the milk). Depending on the final yogurt product, manufacturers will stop the fermentation process in order to produce a firm, stirred or liquid yogurt. Manufacturers have to take into account the viscoelastic properties of the yogurt in their product formulation and production process to reach a specific and constant quality and to improve productivity.

Consequently, there is a need to measure the viscoelastic properties of animal and vegetal milk during the coagulation kinetic. In research and development laboratories, instruments like rheometers are used to characterize the viscoelasticity of milk gels. However, these instruments are not adapted to test the quality of products (both in laboratory and at line) in production environments. Production plants generally use indirect methods to evaluate the viscoelasticity of milk gels. These methods can consist in the measurement, as function of time, of the acidity (pH) or optical properties (light backscatter) of the product. It can also consist in the use of penetrometers that indirectly reflects the overall stiffness state of a product. These methods lack specificity, reproducibility and precision. In some cases, the human expertise is the only one able to evaluate the stiffness of soft gels in plants (case of cheese manufacturers).

In view of the above there is a need for improved, more efficient and more precise methods and tools to measure the viscoelasticity of materials and especially soft materials.

SUMMARY

In an aspect of the invention there is provided a sample holder for measuring viscoelastic parameters of a soft sample comprising a main body comprised of a material having a flexural rigidity, and at least one section comprising a membrane structurally connected to the main body such as to retain the soft sample in the holder and having a flexural rigidity less than that of the main body wherein the soft sample is in contact with the soft membrane, when in vibrations measurements acquisition mode, to form a vibration unit that is configured to allow vibrations and detection of vibrations enabling viscoelastic parameters of the soft sample to be derived.

In another aspect there is provided a system for measuring viscoelasticity of a soft sample comprising a sample holder as described above, a vibration actuator configured to communicate a force to the vibration unit to generate vibrations therein, a vibration detector configured to acquire measurements of vibrations of the vibration unit, and a processor for analyzing the measurements of vibrations obtained from the vibration detector to provide viscoelasticity parameters of the soft sample.

In yet a further aspect there is provided a method for measuring viscoelastic parameters of a soft sample, the method comprising providing a sample in the sample holder as described above, applying a force to induce vibrations in the vibration unit, detecting the vibrations from the vibration unit to provide vibration measurements, and deriving at least one viscoelastic parameter of the soft sample based on the vibration measurements.

In an embodiment of the invention there is also provided a process for manufacturing a product comprising providing a manufacturing system configured to transform an input material into the product, wherein the transformation comprises one or more stages at which one or more viscoelastic properties of the material are required, and measuring the viscoelastic properties.

BRIEF DESCRIPTION OF THE DRAWINGS

The invention will be better understood by way of the following detailed description of embodiments of the invention with reference to the appended drawings, in which:

FIG. 1C is a front elevation sectional view of a device with a pipette or any other filling system used to fill a sample holder with a material;

FIG. 1E is a front elevation sectional view of a device for the viscoelastic characterization of a sample from the vibration of a variant embodiment of the sample holder;

FIG. 1G is a front elevation sectional view of a device for the viscoelastic characterization of a material under manufacturing in a real-time industrial process using a robot and a filling system or any other manual or automatic system.

FIG. 2A is an illustration of a cylindrical sample holder containing the material sample;

FIG. 2B is a cross-sectional illustration of a cylindrical sample holder containing the material sample;

FIG. 2I is an illustration of a dual-sample cylindrical sample holder containing two material samples;

FIG. 2J is a cross-sectional illustration of a dual-sample cylindrical sample holder containing two material samples;

FIG. 2L is a perspective view of a sample holder on a support;

FIG. 2M is a cross-sectional view of the sample holder/support of FIG. 2L;

FIG. 2P is a perspective view of a sample holder encased in a support;

FIG. 2Q is a cross-sectional view of the sample holder/support of FIG. 2N;

FIG. 3D is an illustration of a cylindrical single-sample or a cylindrical dual-sample sample holder at rest in single-cantilever configuration, and a rotational actuator or any other rotating system;

FIG. 3E is an illustration of a cylindrical single-sample or a cylindrical dual-sample sample holder during the impact or the contact between the end side of the sample holder and the rotating system;

FIG. 3F is an illustration of a cylindrical single-sample or a cylindrical dual-sample sample holder during free vibration after the impact or the contact between the end side of the sample holder and the rotating system;

DETAILED DESCRIPTION

In the present description the term soft is used to describe materials having shear elastic modulus lower than about 100 GPa (100,000,000,000 Pa). A soft material may comprise materials in a liquid state. A rigid material is a material that does not detectably vibrate in response to a force applied as will be described further below.

In one aspect of the invention a system that allows sensitive, reproducible and precise viscoelastic properties to be determined is provided in which a sample-sample holder vibration unit enables the measurements of vibration properties (resonance, attenuation, amplitude etc. . . . ) over a range of sample stiffness that lend themselves to direct calculations of viscoelastic properties and/or the establishment of correlations between sample stiffness and the properties.

The device for measuring viscoelastic properties of soft materials according to the invention comprises a sample holder having specific flexural properties in order to confer the vibrating system the required vibration flexibility. The sample holder comprises a flexible membrane connected to a main body or a wall or walls having a higher flexural rigidity than the membrane. It will be understood that the term membrane is meant to refer to the part of the sample holder exhibiting a lower flexural rigidity. As such the membrane may be a unit in itself, either made of the same or different material than the main body and attached to the main body of the holder or alternatively the membrane and the main body of the holder may be made from a continuous block of material but with the membrane area having a smaller thickness to confer a lower flexural rigidity.

Thus the main body or wall(s) of the holder may be made of stiff or hard material. It will be appreciated that the dimensions of the main body or the membrane such as thickness, height and volume influence their flexural rigidity.

In one embodiment the membrane may be likened to a plate for which the flexural rigidity can be defined by:

$$D = \frac{Eh_e^3}{12(1-v^2)}$$

where E is the Young modulus of the material, h is the thickness of the plate and v is the Poisson ratio of the material.

During measurements the membrane is in contact with the sample and a force actuator is used to transmit a force to the sample in the sample holder such as to generate a vibration of the sample and the membrane. The system further comprises a vibration detector and a processor to acquire and process the vibration measurements to provide viscoelastic properties of the sample.

Figure 1A:
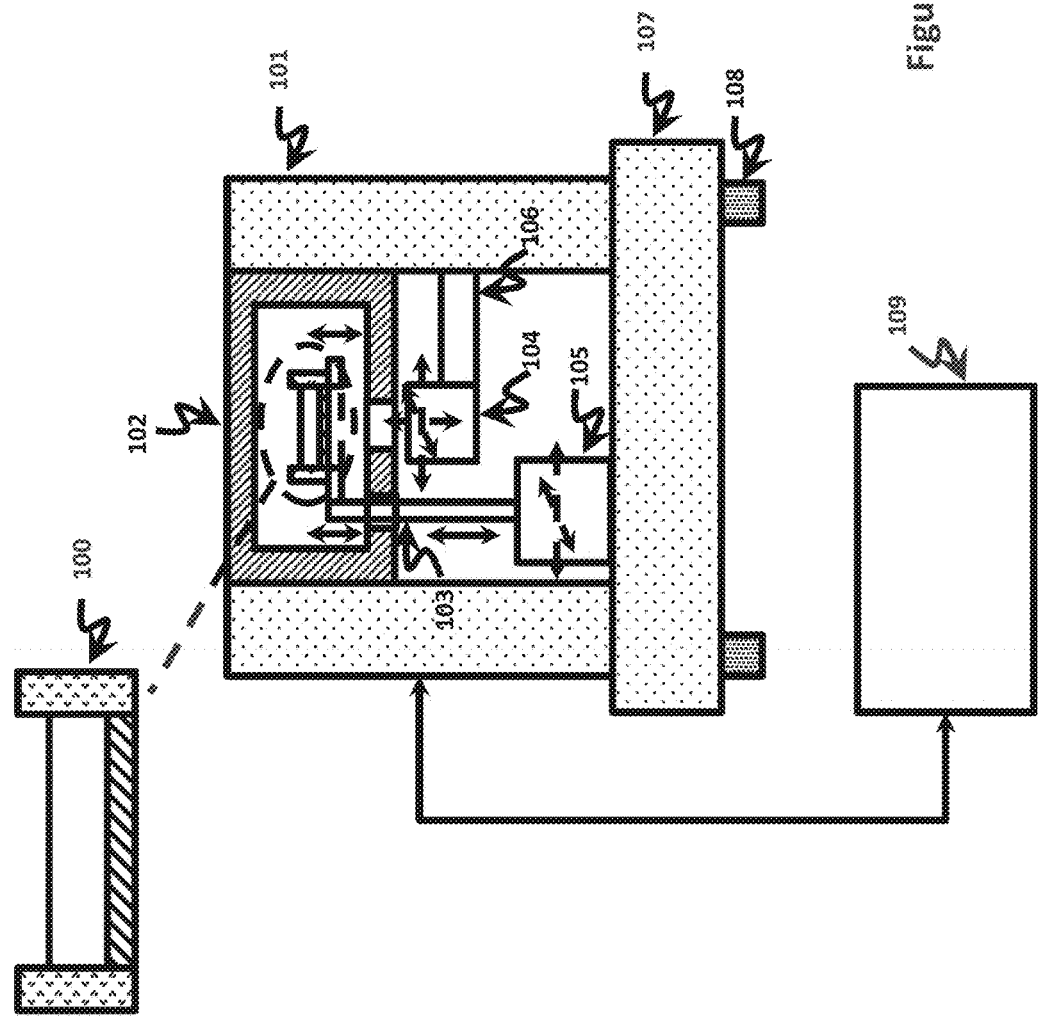
FIG. 1A is a front elevation sectional view of a device for the viscoelastic characterization of a sample from the vibration of the sample holder.

In certain embodiments the entire sample holder may also be induced to vibrate (as for example in embodiments depicted in FIGS. 1A to 1 H and 3D to 3I). In such cases the excitation is transferred to the sample holder through structures such as a rigid bar 103 as will be described further. Thus it is an indirect excitation of the membrane-sample vibration unit which may exhibit vibration frequencies or resonances that are different from the vibration of the holder as a whole. Nevertheless the vibration of the membrane-sample unit can be measured independently by focussing the detector on a part of the vibration unit.

The technology is based on the use of a vibration unit to measure the mechanical properties of soft viscoelastic materials. The vibration unit comprises rigid in flexion sides and at least one area that is more flexible comprising the membrane, which possesses known mechanical and geometrical properties, and a sample of unknown mechanical properties. The membrane is connected to the rigid part of the sample holder. When the material is liquid or very soft, the membrane ensures the sealing of the sample holder. From a mechanical point of view, the vibrations detected following the application of a force will be the vibrations of the combined membrane plus sample. From these measurements, either from correlation measurements (such as standard curves) or model simulations, it is possible to derive viscoelastic properties of soft materials. Theoretical models such as finite element method, finite differences method and analytical models used to derive the viscoelastic properties of material based on vibration response of the material are well known in the art. It will be appreciated that the viscoelastic properties of the membrane can be derived without the presence of the sample so that these known properties can be used in deriving the unknown properties of the sample from the measurements on the vibration unit (sample plus membrane).

FIG. 1A gives an example of an embodiment of the device. The device comprises a rigid and anti-vibration frame 107 supported by vibration insulation feet 108 or any other motion insulation system. A rigid bar 103 connected to the vibration source 105, which is mounted on the frame, transmits the vibration to the sample holder 100. A laser sensor 104 to measure displacement, or any other system to measure the motion, pressure, velocity or acceleration of the vibration, is used to measure vibration of the vibration unit through the vibration of the soft membrane at the bottom of the sample holder, and is positioned in a three-dimensional volume using an actuator 106 or any other positioning system connected to the structure 101. Optionally, the sample in the sample holder can be enclosed in an environmental chamber 102 to control and allow regulation in real-time of environment parameters such as gas composition (oxygen concentration for example), temperature, humidity, or any other environment parameter. The device is controlled, regulated, monitored and configured with the processing unit 109 in order to control, regulate, measure, calibrate, amplify, condition the signals, calculate, process, store, share, interface and/or display measured data.

Figure 1B:
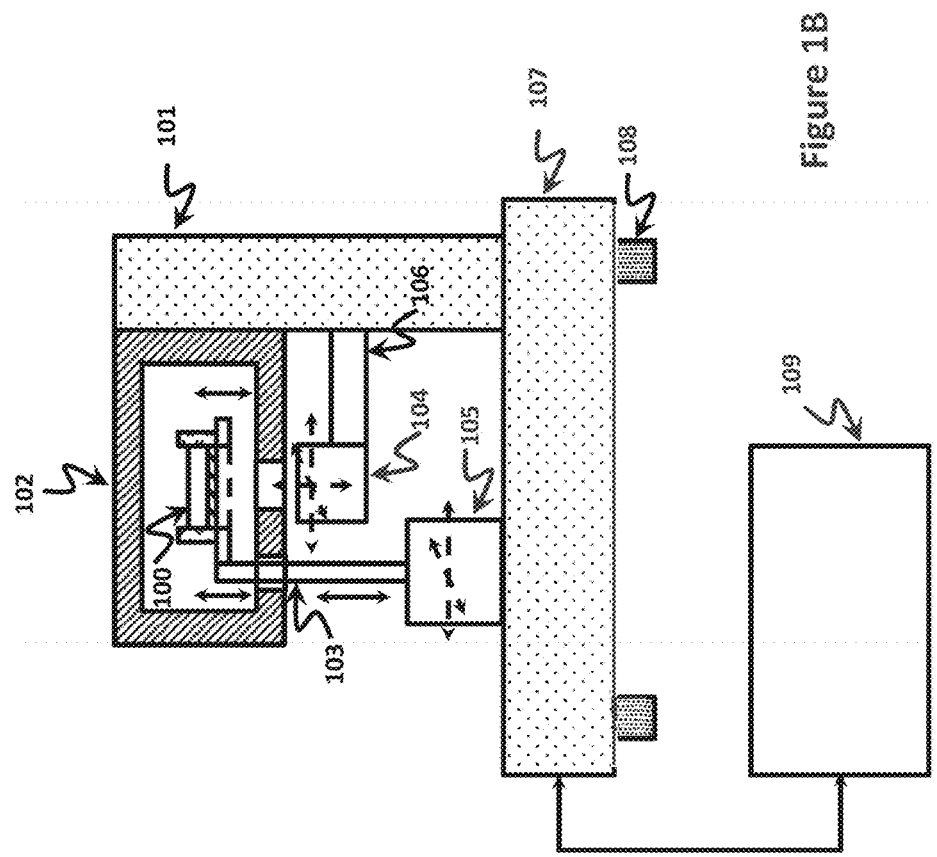
FIG. 1B is a front elevation sectional view of a variant embodiment of the device.

It will be appreciated that variations of the device as shown in FIG. 1A are possible. For example, it is possible to have an "open" system as shown in FIG. 1B. Furthermore the system may also comprise means to insert or inject samples in the sample holder. For example, FIG. 1C shows a two-dimensional front elevation sectional view of a variant embodiment of the device where a pipette or any other filling system 110 is connected to an actuator or dispensing tool 111 which is automatically or manually controlled to position the filling system close to the sample holder.

Figure 1D:
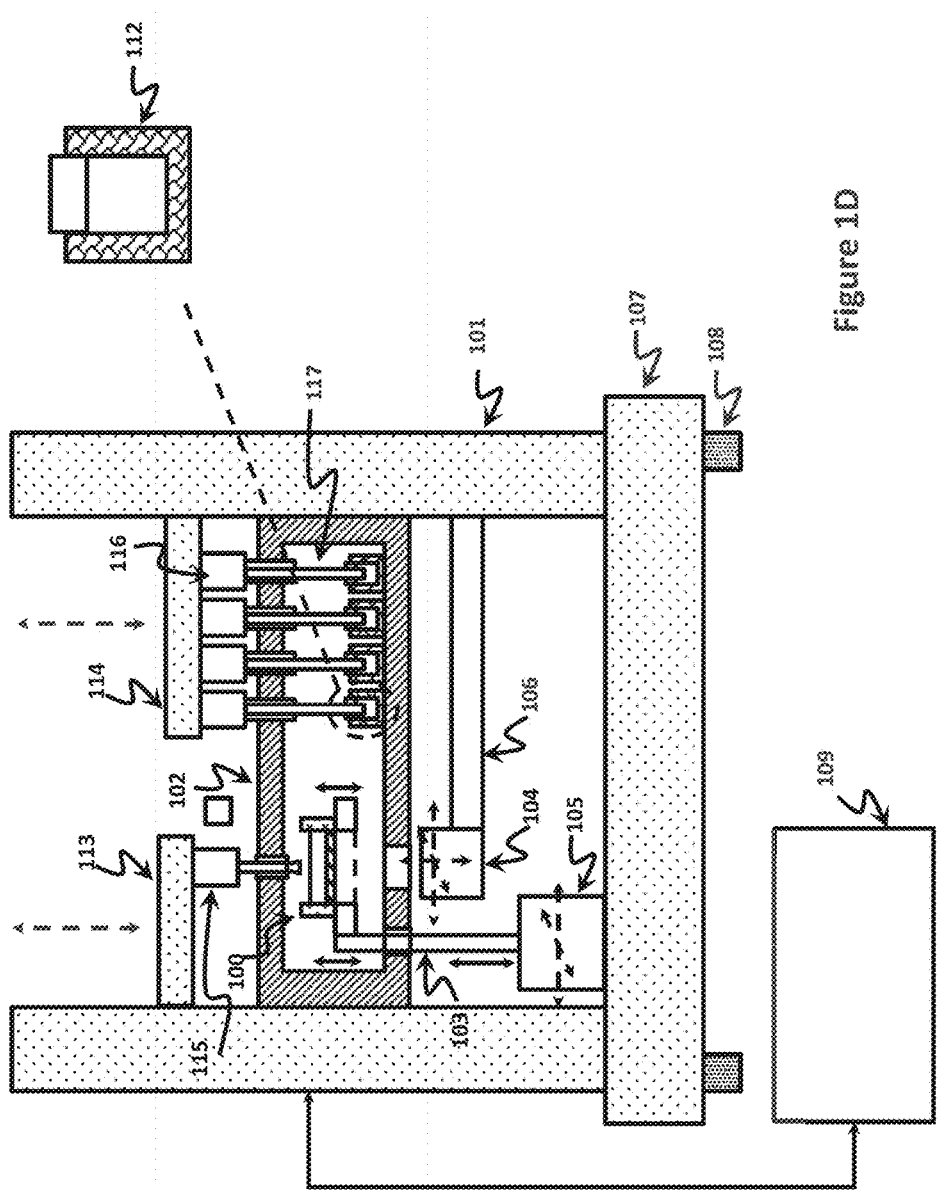
FIG. 1D is a front elevation sectional view of a device including a viscoelastic material measurement and other parameters given by several contactless sensors or with sensors in contact with material sample poured into a static holder.

As mentioned above the environment of the chamber in which the measurements are taken can be controlled. In addition or alternatively sensors and emitters can also be used to monitor and control the sample parameters before and during measurements. FIG. 1D is one possible embodiment of an arrangement of sample parameters sensors showing a front elevation sectional view of a device including sensors for the measurement of parameters like the acidity (pH), the temperature, the humidity, ultrasound velocity and attenuation, the color or any other physicochemical properties. The sensor 117, connected to a pre-conditioning unit 116 for the signal conditioning, is directly in contact with the material sample contained in a container 112, and can be moved vertically using a linear stage 114 or any other translation system. One or more sensors or emitter can also be used to measure or modify physico-chemical parameters when the sample is in the sample holder for measurements. For example, sensor or emitter 115 performs, optionally without contact, the measurements (e.g. camera, microscope, temperature sensor, etc.) or the modification (e.g. source of light, electromagnetic field, electrical field, etc.) of the physicochemical properties of the material sample contained in the sample holder. This sensor can be displaced using stage 113 or any other translation system.

FIG. 1E illustrates a two-dimensional front elevation sectional view of a variant embodiment of the device where the sample holder 100 is connected to a rigid element 119 through an elongated member 118. The sample holder 100 connected to the rigid element 119 through elongated member 118 in a single-cantilever configuration can be submitted to a gentle vibration to induce vibration of the vibration unit.

Figure 1F:
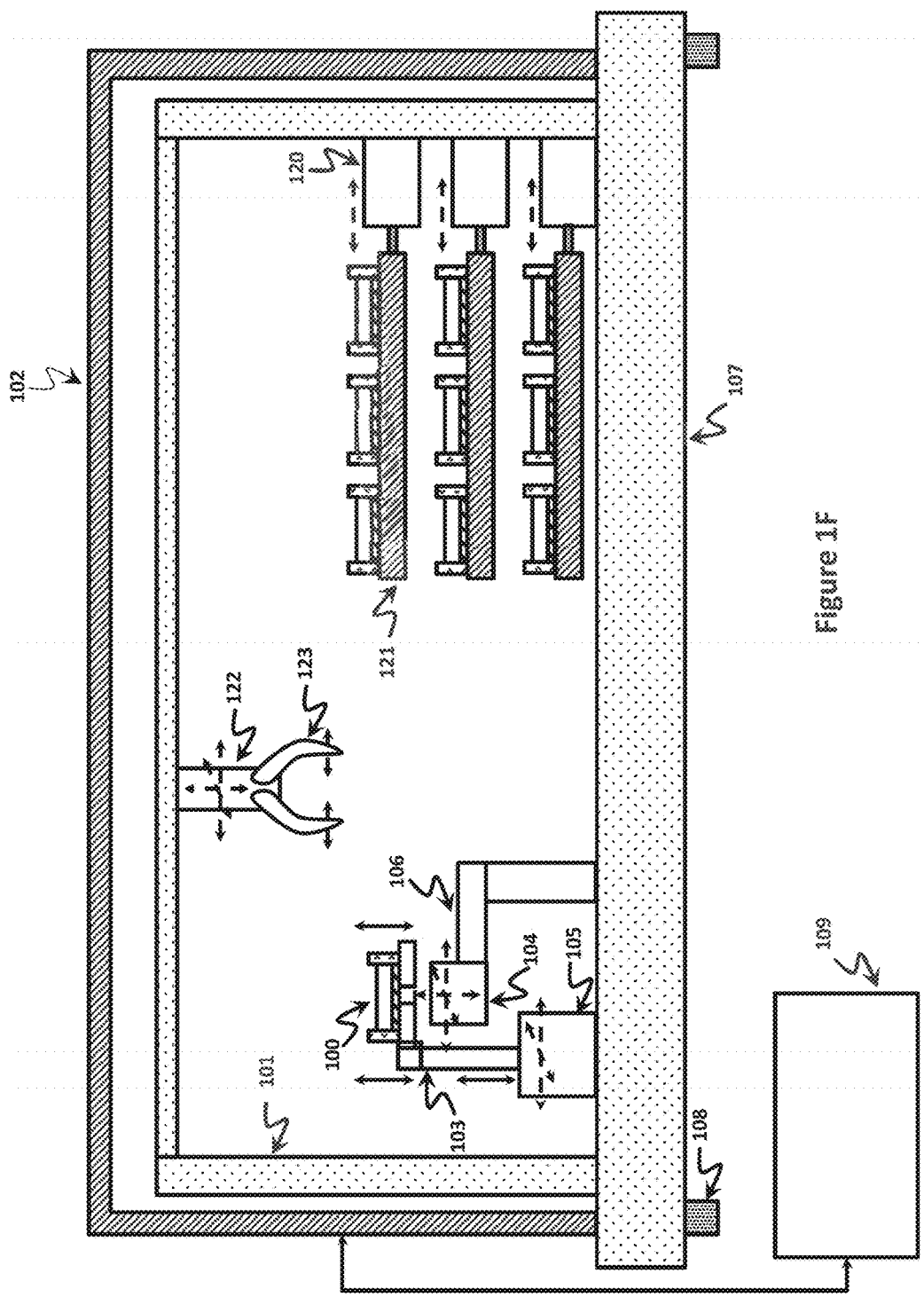
FIG. 1F is a front elevation sectional view of a device for the viscoelastic characterization of a bank of samples positioned into sample holders and automatically handled by a robot or any other automatic system.

The device of the invention can be advantageously adapted for automated repetitive measurements. Various robotic devices as would be known in the art can be used to manipulate samples and/or sample holders to automatically position the sample to acquire vibration measurements. FIG. 1F gives an example of a configuration of an automatic or semi-automatic device which consists in a bank of sample holders organized and stored in a controlled environment and positioned on plates or supports 121, which can be moved by a linear actuator 120 or any other translation system. Any sample holder can be handled and positioned on the measurement station using, for example, an automatic robot gripper 123 positioned in space with an actuator system 122. The vibration generated by the vibration source 105 is transmitted to the sample holder through the rigid connecting bar 103.

In another embodiment of automation, FIG. 1G presents a device beside the process line 124 for the measurement of viscoelastic properties of a sample during and after the manufacturing process. An input conveyor 126, or any other handling system, feeds the filling station with empty sample holders while an output conveyor 127 removes the filled sample holder already tested mechanically. When the empty sample holder is located at the filling station, which is below the filling system 125, a pre-defined amount of material sample is poured into the sample holder and an automatic robot gripper 123, that can moves in a three-dimensional space with an actuator system 122, load the measurement station. Then a vibration is transmitted to the sample holder and the resulting vibration of the vibration unit is measured on the bottom surface of the sample holder to extract the viscoelastic properties of the material sample.

Figure 1H:
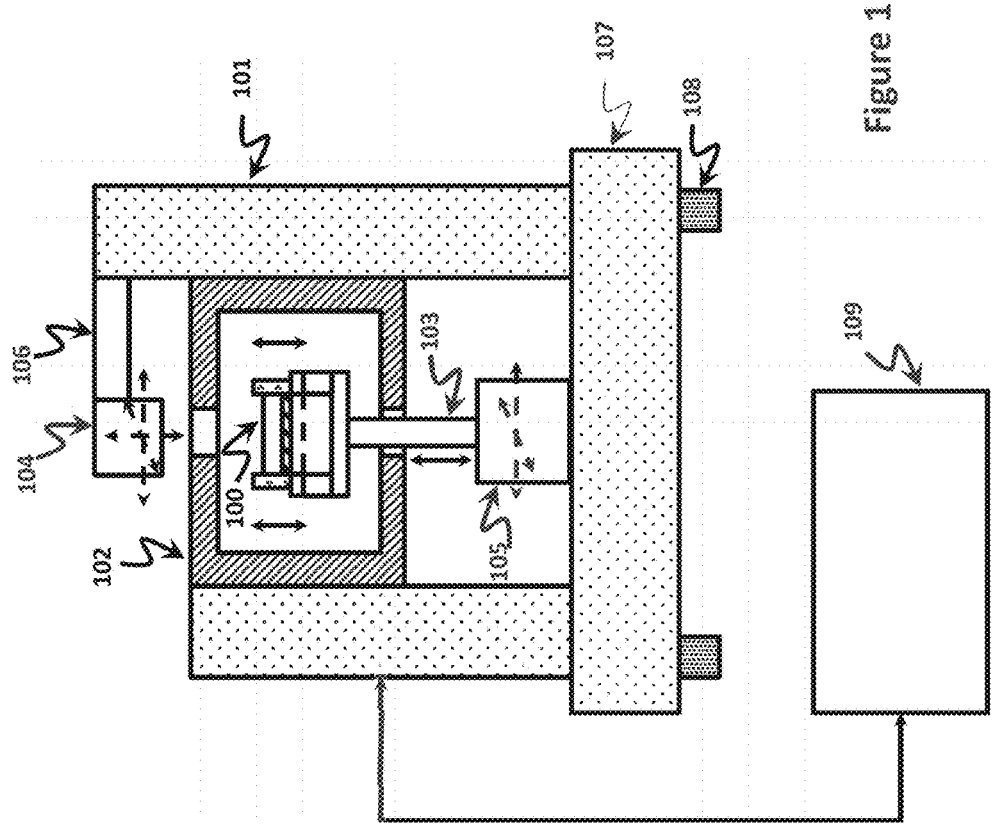
FIG. 1H is a front elevation sectional view of a device for the viscoelastic characterization of a sample from the vibration of the sample holder having a sensor at the top.

Detection of vibration: The detection of the vibration from the vibration unit can be effected in a contact-less manner or by direct contact with the vibration unit. The previous examples have described a contact-less detection in which a laser, capable of measuring displacement of an objet, is positioned below the sample holder such as to measure displacements of the soft membrane which results from the vibration of the vibration unit induced by the force generator. FIG. 1H a two-dimensional front elevation sectional view of a variant embodiment of the device is shown where the laser displacement sensor 104, or any other system to measure the motion, pressure, velocity or acceleration of the vibration, is positioned above the sample holder to acquire the vibration measurements of the vibration unit from the surface of the sample.

While the contact-less detection configuration does provide advantages in terms of design flexibility of the device, it will be appreciated that the vibration measurements can also be performed by placing detector(s) directly in contact with the sample or the soft membrane such as by placing detector(s) on the material sample surface, within the material sample, or on the bottom or upper surface of the membrane or from any other region of interest providing the vibration information of the vibration unit.

The nature of the detector(s) may be selected to suit a particular type of sample measurement and may depend on the degree of sensitivity required, whether contact-less or contact detection is used, the dynamic response characteristics that are required, physical characteristics of the sample etc. . . . . Detectors may be selected from optical, laser, magnetic field detector, gas pressure detector, piezoelectric sensor and combination thereof as would be known to one skilled in the art. Preferably the detector is configured to detect vibrations over a range of frequencies.

Sample holder: In an aspect of the invention there is provided a sample holder in which the sample is placed to perform the vibrations measurements. The sample holder comprises a main body 200 substantially made of rigid material and a section comprising a soft membrane. In an embodiment the soft membrane constitutes the bottom of the holder as shown in FIG. 2A (201). The membrane is attached to the rigid structure. In the case of very soft samples or liquid samples, the membrane is sealed to the rigid main body. When the sample is in the holder it forms, together with the membrane, a vibration unit. When a vibration is transmitted to the sample holder, the vibration unit 'membrane/sample' vibrates under the action of the excitation and its inertia. Therefore the detection of vibrations will reflect the viscoelastic properties of the membrane and the sample.

When the vibration excitation is transient, the system vibrates under the action of its own inertia. Depending on the direction of the force vectors applied to the sample holder, the resulting vibration may exhibit different directional components. In one example, the vibration unit may vibrate vertically in bending mode. The free vibration of the unit can exhibit resonances. The temporal or frequency characteristics of these resonances depend on the mechanical and geometrical properties of the vibration unit. The vibration modes for example may comprise free linear vibrations, forced vibrations and the like.

Since the geometry of the vibration unit and the mechanical properties of the membrane are known, the viscoelastic property of the sample is the only unknown contributing to the resonant vibration. Any model simulating the vibration of the vibration unit can be used to determine the viscoelastic properties of the sample from experimental measurements. For example, the resonance frequency of the system can be related to the shear elasticity of the sample.

The mechanical/viscoelastic properties of the membrane influence the quantitative and qualitative nature of the vibrations detected from the vibration unit. This latter has to be soft enough to deform and vibrate under the action of its inertia or applied force. In the limit case where the membrane is rigid (very high stiffness), the system will not vibrate and resonate as described previously. At the opposite, when the membrane is very soft, the system can present an excessive static bending, and the vibration of the unit can be unstructured. This can prevent the use of the bending vibration to measure the viscoelastic properties of the sample.

The unique combination of the membrane-sample vibration unit enables the system to acquire vibration characteristics, in terms of precision, sensitivity, reproducibility to an extent that is not possible with systems of the prior art in which the sample holders are not allowed to exhibit the range and characteristics of vibration modes afforded by the sample holder of the present invention.

The membrane exhibits a shear elastic modulus preferably in the range of between 1 kPa to 100 GPa. More preferably, the membrane shear elastic modulus should be comprised between 10 kPa and 100 MPa. It will be appreciated that the desired characteristics of the soft membrane may vary according to the nature of the sample being measured.

The frequency and amplitude of vibrations of the membrane will depend on its flexural rigidity. This latter has to be selected by taking into account the mechanical and geometrical properties of the tested sample, the lateral dimensions of the membrane and the sensitivity (precision) of the sensor used to measure the vibrations of the vibrating system. The flexural rigidity of the membrane should allow an amplitude of free linear vibration, at its frequency of resonance, of about at least 1 micro-meter. The maximum free linear vibration amplitude of the membrane, at the resonance frequency, should preferably not exceed 25% of its greatest lateral dimension.

One role of the membrane is to provide necessary sealing when the material sample is very soft or liquid. The membrane also allows to structure the vibration of the vibration unit and to enhance the vibration dynamic when materials are very soft. The relative contribution of the membrane and the sample to the vibration of the vibration unit depends on the relative viscoelastic properties of each. For example, the elasticity of the sample can exceed the elasticity of the membrane. Is this case, the overall vibration of the vibration unit will be dominated by the vibrational behavior of the material sample.

The membrane plays an important role in the detectability limit of the device, i.e. the smallest value of viscoelasticity that can be measured by the device. For a very soft material, a softer membrane will decrease (improve) the detectability limit of the device. Inversely, harder membranes will increase the value of minimum measurable viscoelastic properties. The membrane thickness has also an important role in the definition of the detectability limit. For otherwise equivalent viscoelastic properties, a thick membrane decreases the detection limits, while a thin membrane improves it. Thus it will be appreciated that the characteristics of the membrane, in particular its stiffness and thickness can be adjusted to obtain an optimal vibrational stability, a maximum signal to noise ratio and a maximum detectability for a given sample. It will be appreciated that environmental parameters such as temperature and humidity can influence the viscoelastic properties of the membrane and may be taken in consideration when deriving the viscoelastic parameters of the sample.

The sample holder will now be described in more details with reference to exemplary embodiments. A cylindrical sample holder is presented in FIG. 2A, and in the cross-section view FIG. 2B, and consists in a hollow cylinder 200 with a small height compared to its diameter. The flexible soft membrane comprising the bottom 201 is firmly connected to the inner surface of the cylinder. The soft membrane has a relatively small thickness compared to the bottom diameter. The membrane can present a thickness ranging between 1/1000 and 1 times the thickness of the sample as measured when the sample is in the holder. At least one of the lateral dimensions (length for example) of the vibration unit should be ranged between 1 and 100 times the thickness of the vibration unit. For example, a cylindrical sample holder can conform the material and the membrane to form a system with the following dimensions: a diameter of 20 mm, a membrane thickness of 1 mm, a sample thickness of 6 mm.

Figure 2C:
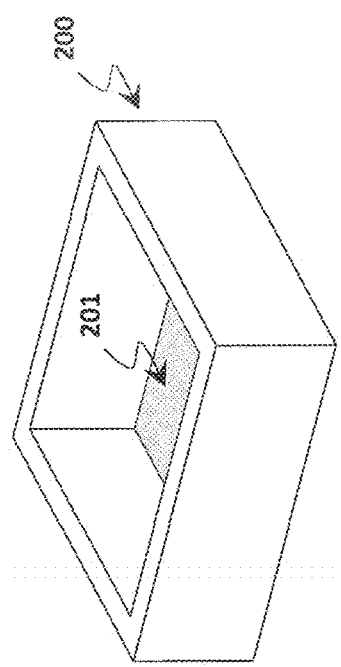
FIG. 2C is an illustration of a rectangular sample holder containing the material sample.
Figure 2D:
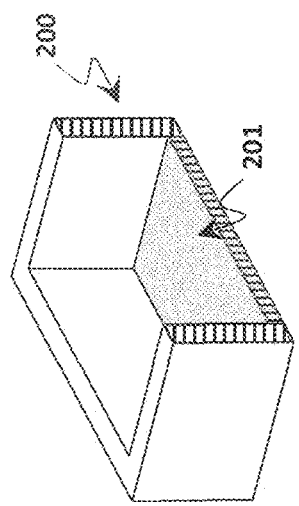
FIG. 2D is a cross-sectional illustration of a rectangular sample holder containing the material sample.

Another configuration is shown as a rectangular sample holder presented in FIG. 2C, and in the cross-section view FIG. 2D, which consists in a hollow parallelepiped with a small height compared to its width and length. The soft membrane at the bottom 201 is firmly connected to the inner surface of the parallelepiped. The soft membrane has a small thickness compared to its two other dimensions.

Figure 2E:
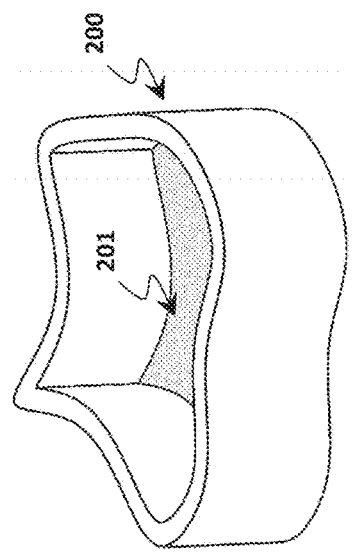
FIG. 2E is an illustration of a sample holder with an arbitrary shape containing the material sample.
Figure 2F:
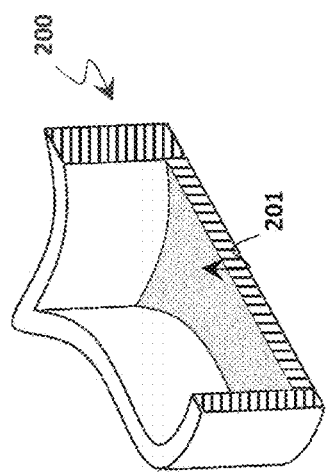
FIG. 2F is a cross-sectional illustration of a sample holder with an arbitrary shape containing the material sample.

More generally, as described in FIG. 2E and FIG. 2F (cross-section view), the sample holder can be defined as a hollowed out volume with any arbitrary and known cross-sections with a small height compared to its other dimensions. The soft membrane at the bottom 201 is firmly connected to the inner surface of the hollowed out volume.

Figure 2G:
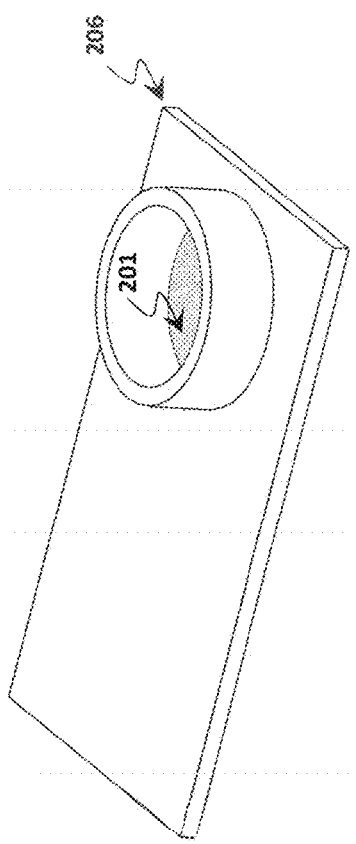
FIG. 2G is an illustration of a single-sample cylindrical sample holder containing one material sample.
Figure 2H:
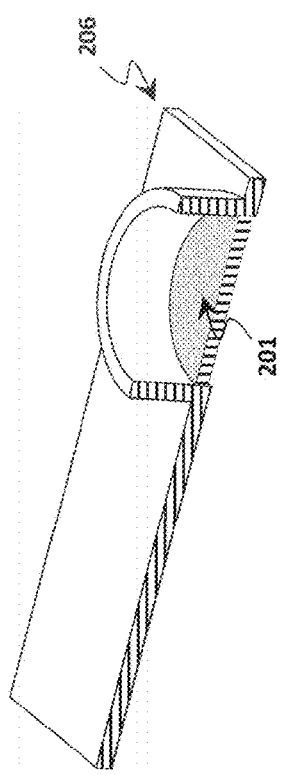
FIG. 2H is a cross-sectional illustration of a single-sample cylindrical sample holder containing one material sample.

FIG. 2G and FIG. 2H (cross-section view) give another configuration of the sample holder which is defined as a cylindrical single-sample sample holder 206 and consists in the fusion of the cylindrical sample holder with a plate. Such an arrangement can be used when vibrations are imparted to the vibration unit by transiently bending the plate vertically. A variation of this embodiment is presented in FIG. 2I and FIG. 2J (cross-section view) as a cylindrical dual-sample sample holder 208. As will be appreciated, more than two sample holders may be used.

Figure 2K:
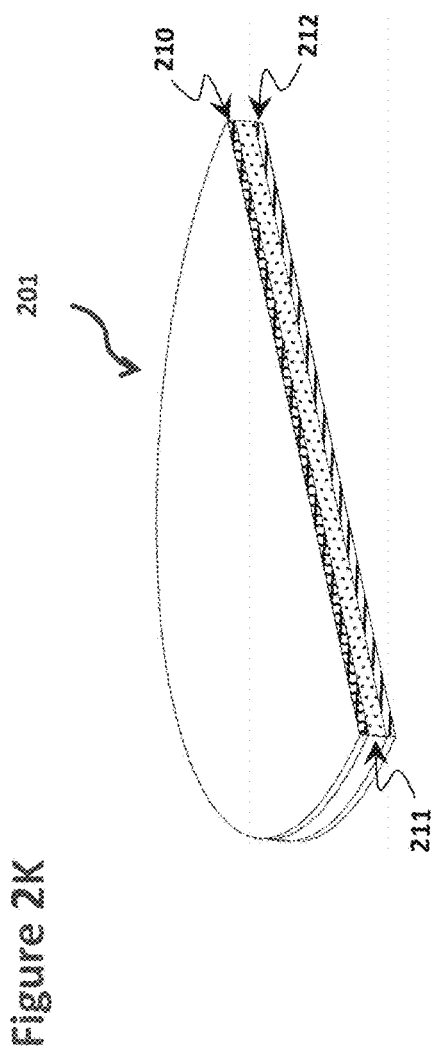
FIG. 2K is a cross-sectional illustration of a membrane with coatings on both sides.

The membrane 201 of the sample holder can be made of soft elastomer, silicon rubber, gel, or any other elastic or viscoelastic material having a shear storage modulus ranging from few kilopascals (1 kPa) to hundreds of gigapascals (100 GPa). The membrane material can be transparent, semi-opaque or opaque, properties that can be exploited for example when it is desirable to see the sample through the membrane or if the amount of light reaching the sample is important for a particular application. The sample holder membrane preferably has a small thickness compared to the diameter or lateral dimensions of the bottom of the sample holder and a small height compared to its diameter or lateral dimensions. With reference to FIG. 2K, the membrane may comprise coatings or components useful for the detection of vibrations. The upper surface of the membrane 210 (in contact with the material sample) can be coated with reagents, medication molecules, enzymes, coagulant agents, biochemical products, living cells or tissues, or any other substances that can chemically or mechanically impact or not the material sample. The lower surface of the membrane 212 can be coated with a thin layer of reflective, metallic, magnetic, or any other material used to perform vibration measurement. The coatings 210 and 212 on either the side facing the sample or the external side are optional. The membrane can also be submitted to a radial tension force.

Figure 2N:
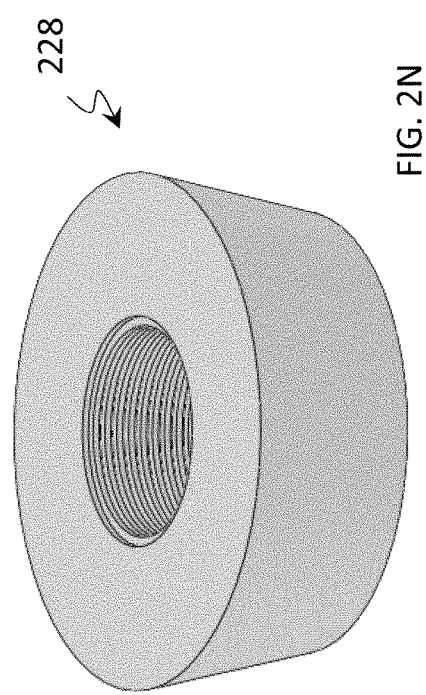
FIG. 2N is a perspective view of a sample holder in which the main body and the membrane are made of the same material.
Figure 2O:
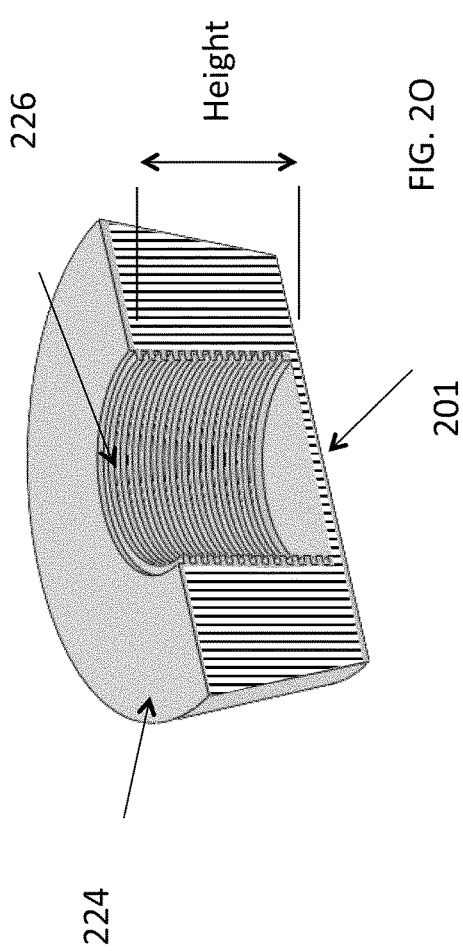
FIG. 2O is a cross-sectional view of the sample holder/support of FIG. 2N.

Additional exemplary embodiments of the sample holder of the invention are shown in FIG. 2L to 2Q in which a perspective view of a cylindrical shaped holder 220 is shown (FIG. 2L) mounted on a support 222 to secure the holder in a proper position within the system. In particular it will be appreciated that the support and the structure with the system to secure the support to are configured to optimize the positioning of the sample holder and the vibrating unit (membrane-sample) with respect to the force actuator and vibration detector. The inner part of the surrounding wall (or main body) of the sample holder can comprise such as threads or annular recesses in order to improve the adhesion of the tested sample to the sample holder and to avoid slipping effects during the testing and the handling of the sample. FIG. 2M shows an example in which the inner face of the wall 224 of the sample holder comprises annular recesses 226. FIGS. 2N and 2O shows a sample holder 228 embodiment in which the main body and the membrane are made of the same material and from a single block. In FIGS. 2P and 2Q another embodiment is shown in which the sample holder is encased in a support 230. It will be appreciated the support may be designed to optimize the flexural rigidity of the sample holder or part thereof.

Figure 3A:
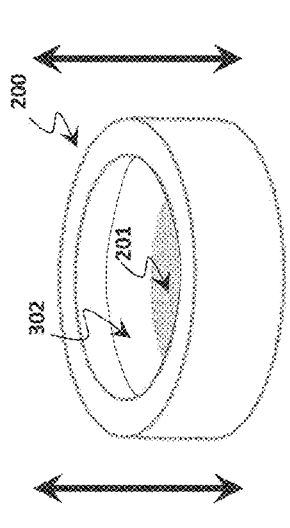
FIG. 3A is an illustration of a material sample contained into a cylindrical sample holder on which is induced a gentle vibration for the characterization of the sample viscoelasticity.
Figure 3B:
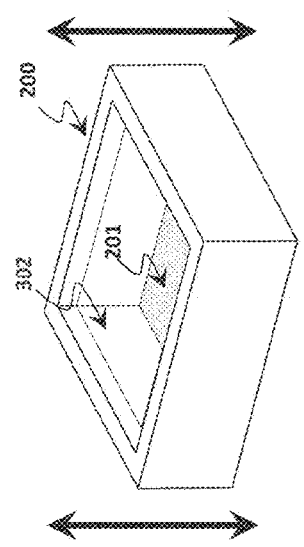
FIG. 3B is an illustration of a material sample contained into a rectangular sample holder on which is induced a gentle vibration for the characterization of the sample viscoelasticity.
Figure 3C:
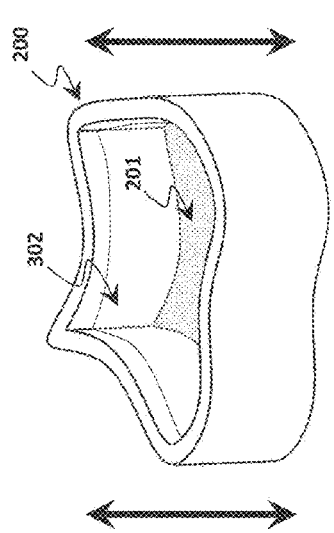
FIG. 3C is an illustration of a material sample contained into a sample holder with an arbitrary shape on which is induced a gentle vibration for the characterization of the sample viscoelasticity.

With reference to FIGS. 3A to 3K various embodiments of vibration excitation configurations will be described. FIG. 3A illustrates a cylindrical sample holder composed of a rigid hollow cylinder and the membrane 201 at the bottom and containing a material sample 302 to be mechanically tested. During a test, a vibration is applied to the sample holder in the aim to induce the vibration of the vibration unit composed by the soft and flexible membrane and the material sample. A composition of waves that propagate inside the vibration unit (sample and sample holder bottom) induces the creation of a vibration having characteristic features in the temporal or frequency domains (resonance frequencies, quality factors, vibration amplitude, damping, . . . ) related to the material sample viscoelasticity. FIG. 3B presents a variation in which the sample holder is rectangular and contains the material sample 302. Yet another variation is shown in FIG. 3C, where the sample holder has an arbitrary and known cross-section.

FIG. 3D, FIG. 3E, and FIG. 3F present another configuration for the vibration generation by inducing the bending of the elongated member 118 to which the sample holder is connected using, for example, a rotating impactor 309. The sample holder, containing the flexible membrane 201 and the material sample 302, is firmly connected in single-cantilever configuration to a static support such as between two static blocks 313 and 314. At rest (FIG. 3D), the rotating impactor 309 does not touch the sample holder, which is in a resting state. The vibration unit is also at rest. When the rotating impactor is in contact with the end of the sample holder (FIG. 3E), this induces the bending of the elongated member 118. When the rotating impactor releases the end of the sample holder (FIG. 3F), the bending vibration of the elongated member 118 generates waves in the vibration unit. A composition of waves that propagate inside this vibration unit (sample and sample holder bottom) induces the creation of vibrations having characteristic features in the temporal or frequency domains (resonance frequencies, quality factors, vibration amplitude, damping, . . . ) related to the material sample viscoelasticity.

Figure 3G:
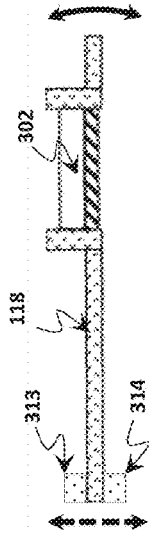
FIG. 3G is an illustration of a cylindrical single-sample or a cylindrical dual-sample sample holder during free vibration after the vertical vibration or the motion of the two blocks firmly connected to the sample holder base.

FIG. 3G gives another configuration of vibration excitation of the sample 302. The elongated member 118 is firmly connected to two blocks 313-314 which are displaced such as to induce vibration. The induced bending vibration of the elongated member is the origin of the wave that propagates inside the material sample and the flexible bottom.

Figure 3H:
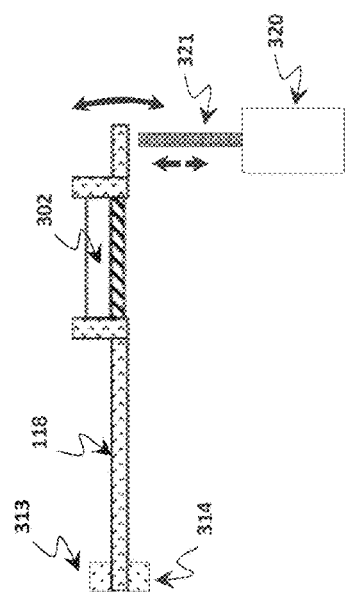
FIG. 3H is an illustration of a cylindrical single-sample or a cylindrical dual-sample sample holder during free vibration after the impact or the contact between the end side of the sample holder and the linear actuator or any other translation system.
Figure 3I:
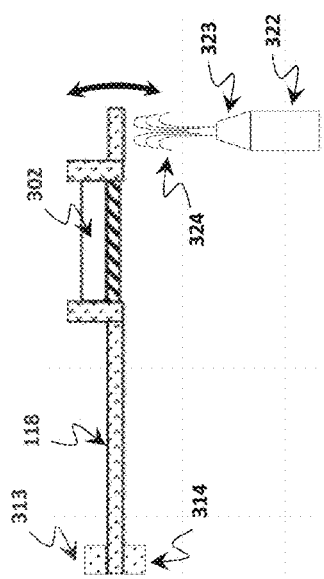
FIG. 3I is an illustration of a cylindrical single-sample or a cylindrical dual-sample sample holder during free vibration after the impact or the contact between the end side of the sample holder and the fast air or water jet or any other liquid or solid substance.

FIG. 3H and FIG. 3I gives two other configurations where the elongated member 118, connected in a single-cantilever configuration between two static blocks 313-314, is mechanically excited either by a bar 321 connected to a linear actuator or any other translation system 320 (FIG. 3H), or by a fast air or water jet or any other liquid or solid substance (such as a projectile) 324 (FIG. 3I). For the latter, the fast jet configuration (shape, etc.) can be adjusted using the nozzle 323 and the flow rate and velocity of the jet can be modified using the system 322. The resulting free bending vibration of the sample holder transmits the vibration to the vibration unit. Another version of this system is a device where the bar 321 is permanently connected to the elongated member 118 during and after the excitation.

The vibration excitation of the vibration unit can be achieved by directly applying the force to the vibration unit through the soft membrane, the sample or a combination of both. In the exemplary configurations presented in FIG. 3J and FIG. 3K a bar 321 connected to a linear actuator or any other translation system 320 (FIG. 3J), or a fast gas or water jet or any other liquid or solid substance 324 (FIG. 3K) are used to induce the vibration by directly contacting the vibration unit.

Figure 3J:
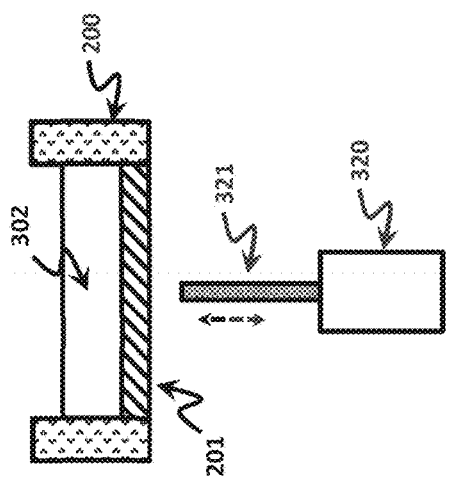
FIG. 3J is an illustration of a cylindrical sample holder during free vibration of the bottom after the impact or the contact between the bottom of the sample holder and the linear actuator or any other translation system.
Figure 3K:
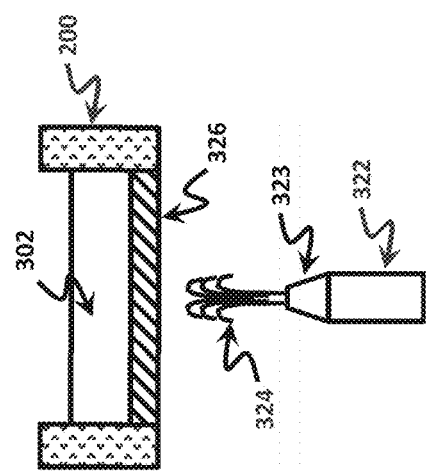
FIG. 3K is an illustration of a cylindrical sample holder during free vibration of the bottom after the impact or the contact between the bottom of the sample holder and the fast air or water jet or any other liquid or solid substance.

It will be appreciated that other configurations for achieving either indirect vibration excitation of the vibration unit as shown in FIGS. 3A to 3I or direct excitation as shown in FIGS. 3J and 3K are also possible as would be known to one skilled in the art.

Figure 4A:
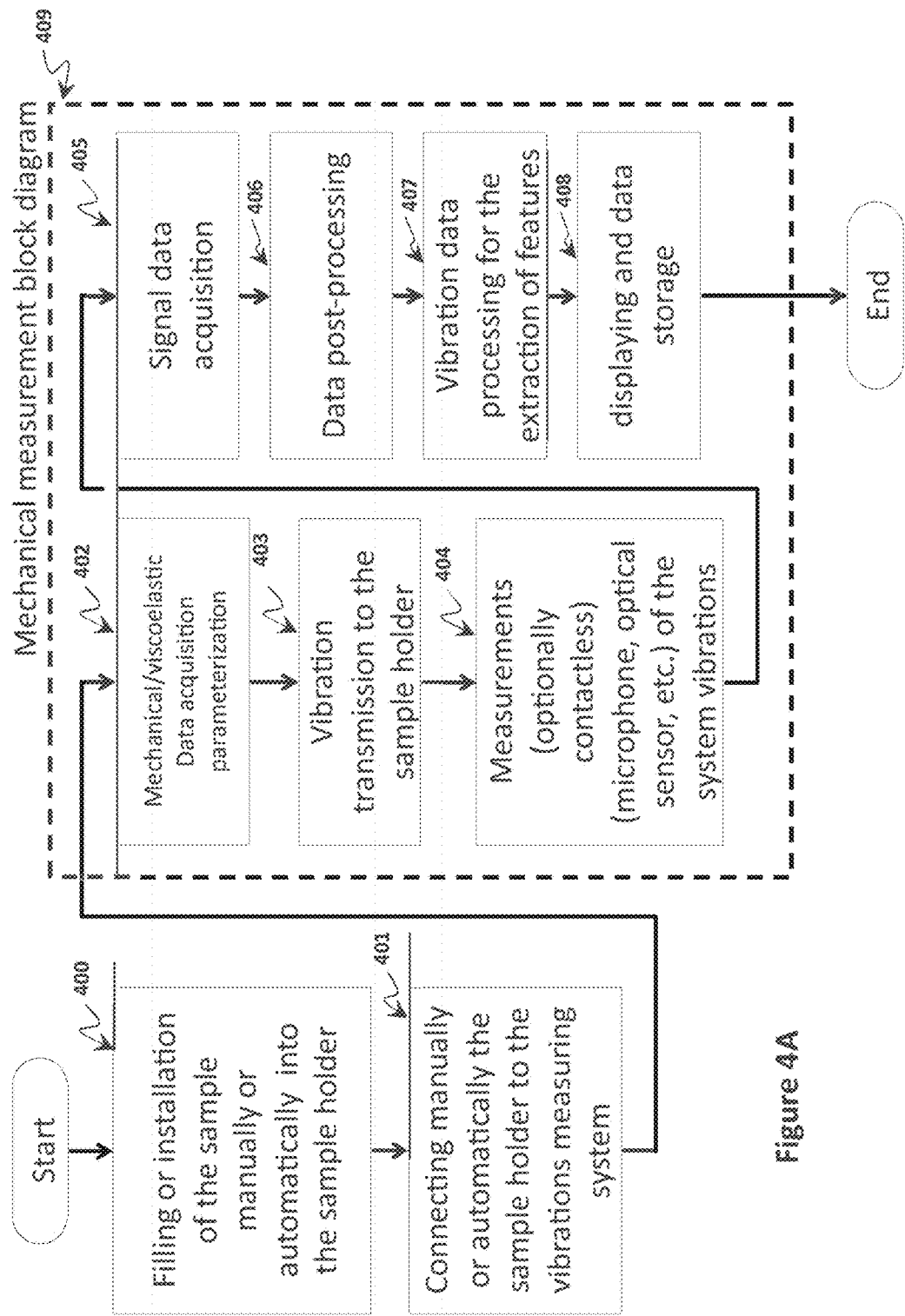
FIG. 4A is a flowchart of a typical protocol for the mechanical (viscoelasticity) measurement of a single material sample using the device.

FIG. 4A is a flowchart of a typical viscoelastic measurement on a material sample using the system of the invention. The first step 400 consists in filling or installing the material sample to test into the sample holder. This operation can be done manually, semi-automatically or automatically. The sample holder, now comprising the vibration unit, is then connected 401 to the device in the measurement station. Alternatively the sample holder may already be in the measurement station and in position for data acquisition when the sample is placed in the sample holder. After mechanical data acquisition parameterization 402 which is the configuration of the system to adjust parameters such as vibration excitation force, duration of excitation, frequency, etc., a vibration is transmitted 403 to the sample holder and a sensor measures (optionally contactless) 404 the vibrations of the vibration unit. This vibration data is acquired 405 and transmitted 406 to the post-processing unit for the signal conditioning. The vibration temporal and spectral data are then processed and features such as the resonance frequencies, the quality factors or the amplitude and damping, or any combination of these features are extracted 407 and serve to characterize the viscoelasticity of the material sample. Finally, the results are either stored, shared or displayed or a combination thereof 408. The steps 402, 403, 404, 405, 406, 407 and 408 define the mechanical measurement block diagram 409 which can integrated in other functionalities of the device.

Figure 4B:
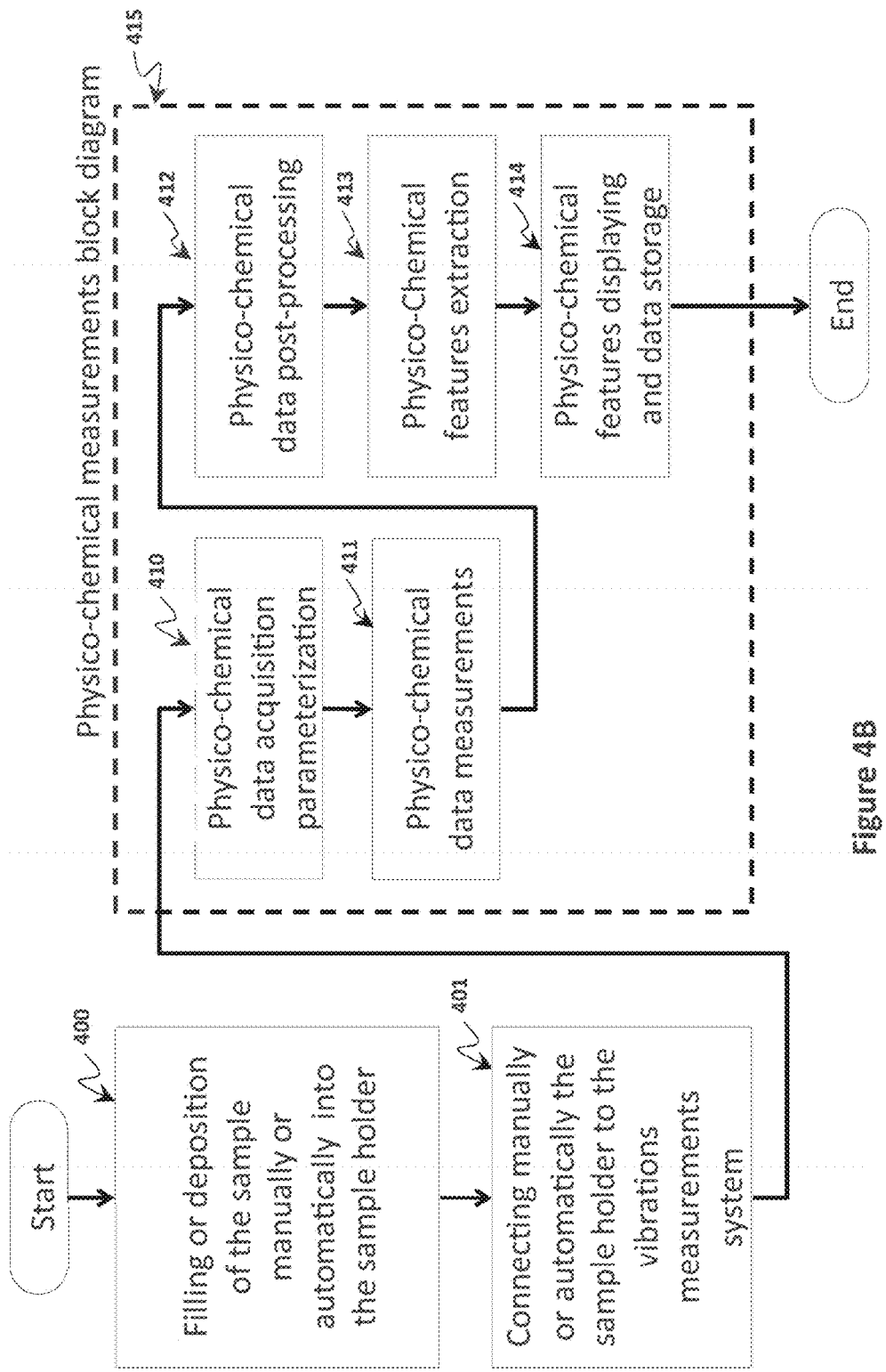
FIG. 4B is a flowchart of a typical protocol for the sensor (pH, humidity, temperature and other information) measurement of a single material sample using the device.
Figure 4C:
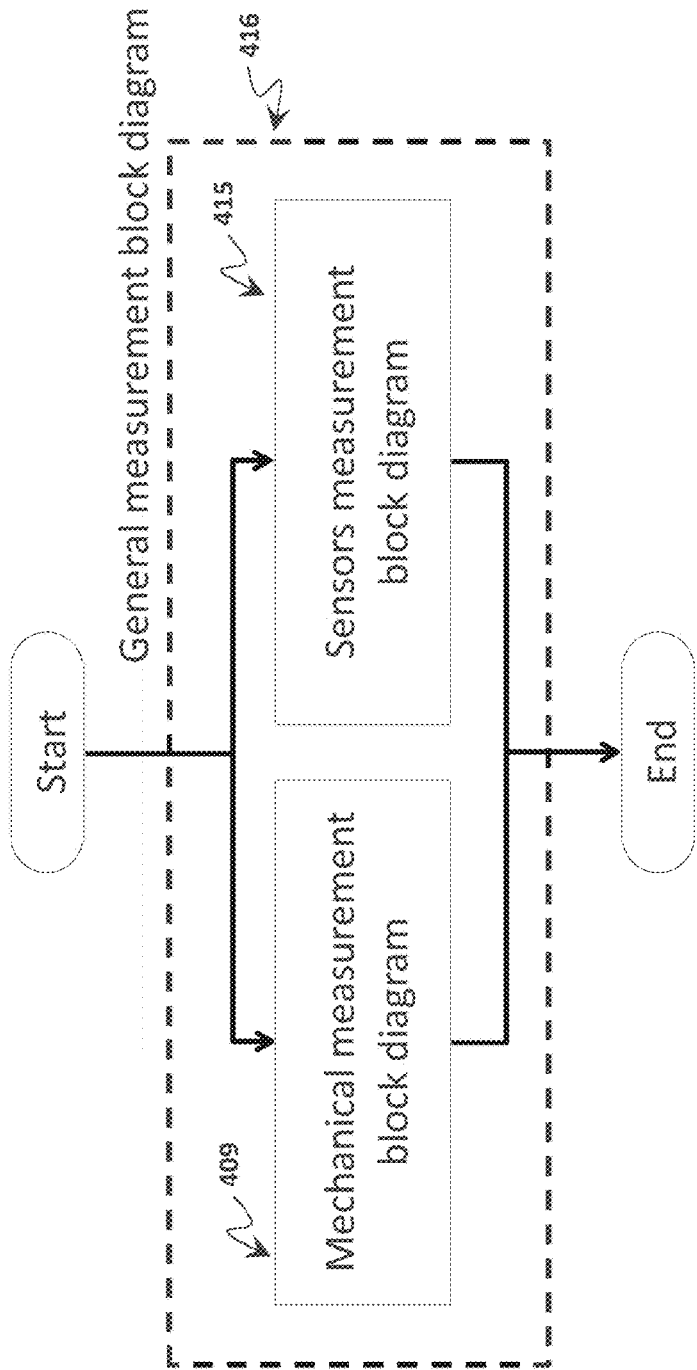
FIG. 4C is a flowchart of a typical protocol for the general (mechanical and sensor measurements) measurement of a single material sample using the device.

FIG. 4B presents a flowchart describing the measurements of physico-chemical parameters data such as temperature, pH, humidity, color and the like of the sample. After dispensing 400 of the material sample into the sample holder and the connection 401 of the sample holder to the device, the physico-chemical measurements block diagram 415, including the steps 410, 411, 412, 413 and 414, is activated. This block diagram describes an exemplary series of steps including parameterization of physico-chemical parameters acquisition 410, the actual measurement of the parameter(s) 411 and the signal post-processing 412 to condition the raw data. Several features of the parameter(s) are then extracted 413 such as the evolution over time, the activation time, phases identification and characterisation, the maximum and minimum values, the increasing or decreasing rate or any other features describing the kinetics of the measured parameter(s). Finally, the results are stored, shared and/or displayed 414. These data may be can be acquired simultaneously, as shown in FIG. 4C where a flowchart describes a general measurement block diagram 416 composed of the mechanical measurement block diagram 409 and the sensors measurement block diagram 415, with the vibrations measurements. Accordingly, the system and methods of the present invention can enable the real-time combination of viscoelastic measurements and physico-chemical parameters thereby increasing the amount of information that can be used to characterize a product or control its production.

Figure 4D:
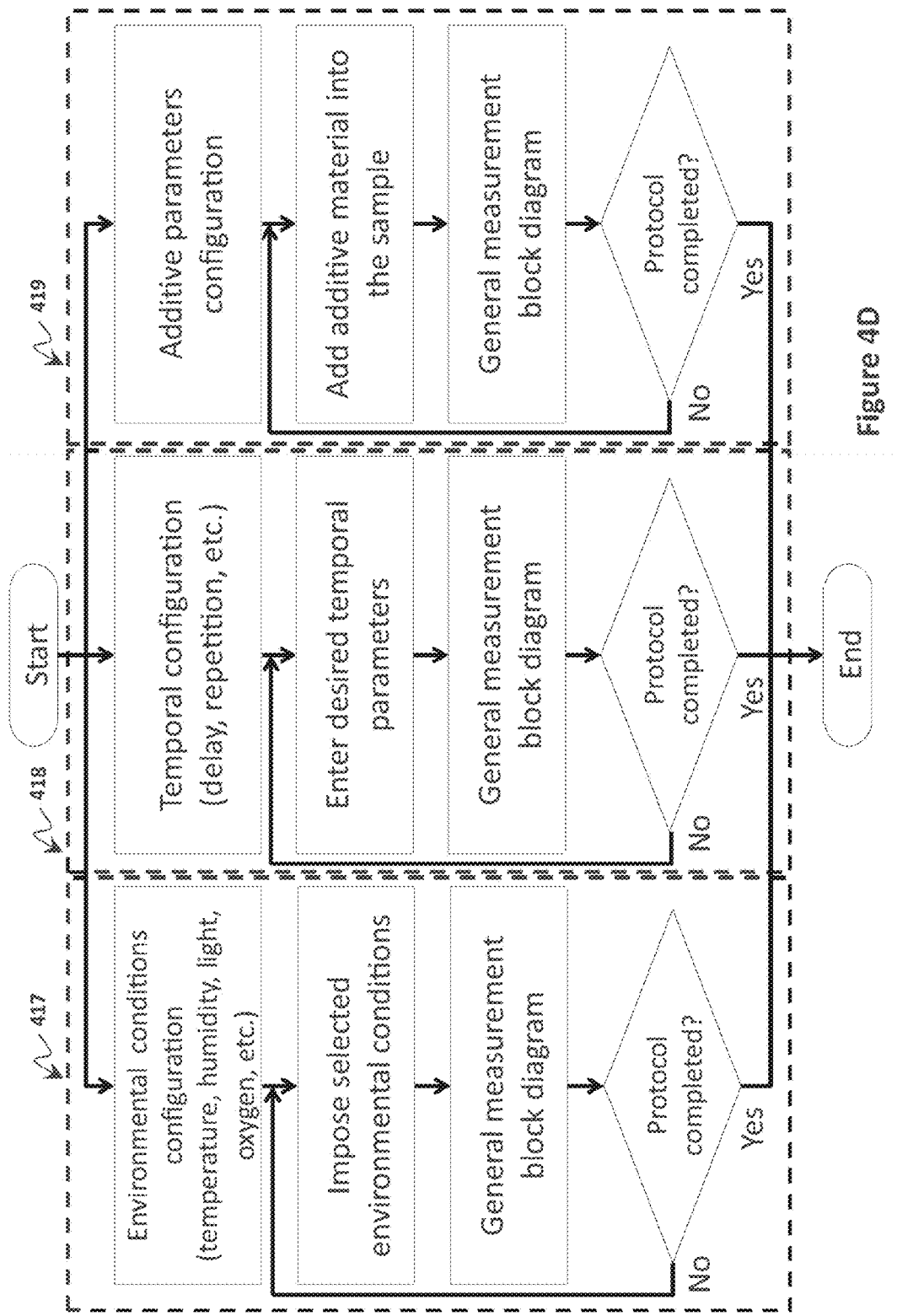
FIG. 4D is a flowchart of general measurements (mechanical and sensor measurements) as function of environmental conditions, temporal and additive parameters configurations using the device.

FIG. 4D is a more detailed flowchart that presents different configurations of data acquisition and treatment. The steps included into the group 417 allows configuring the environmental conditions of the test such as the temperature, the humidity, the light, the oxygen content, or any other environmental conditions. The second configuration 418 is related to the time parameters and allows configuring the delay between acquisitions, the number of acquisitions, or any other temporal conditions. The third configuration 419 is related to the additive parameters that can be mixed or added to the material sample before, during and after the material characterization. For example, reagents, medication molecules, enzymes, coagulant agents, biochemical products, living cells or tissues, or any other substances of interest. All the above-mentioned configurations can be interlinked with each other (example: a change in temperature may trigger addition of a reagent) and are repeated until all the pre-defined environmental conditions are sequentially satisfied. Several features are then extracted like the evolution over time of viscoelasticity, the activation time, phases identification and characterisation, the maximum and minimum values, the increasing or decreasing rate or any other features describing the measured kinetic. Finally, the results are stored, shared and displayed.

Any soft material can be analyzed using the system of the present invention. In particular, soft material found in the food industry such as milk and milk derivatives (curd, cheese, tofu, yogurt and the like) as well as biological samples such as blood (including blood at different stage of coagulation) and biomaterials. By biomaterial it is meant any soft biomaterials such as tissues including cell cultures, skin cultures, natural or artificial blood vessels and the like. Certain designs of the system of the present invention, such as contactless detection of vibrations, may facilitate the viscoelastic properties measurements of biological samples under sterile conditions. Other types of materials that can be measured include without being limited to: polymers, silicones, pharmaceutical products, pharmaceutical excipients, resins, elastomers, gels, plastics and the like. Advantageously the system of the invention can be used for the development, manufacture and quality control of the materials mentioned above.

Figure 4E:
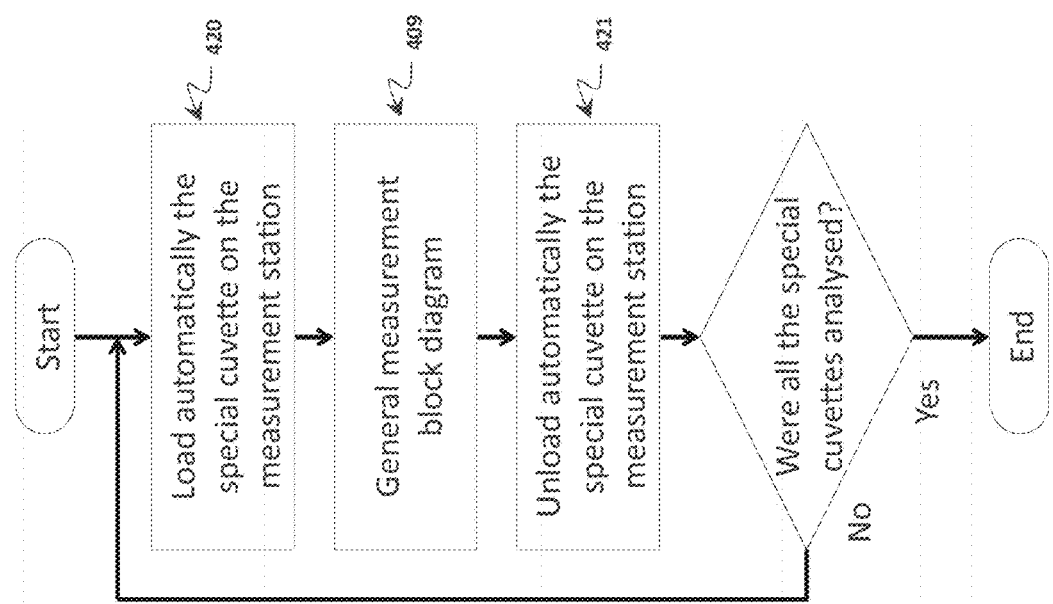
FIG. 4E is a flowchart of general measurements (mechanical and sensor measurements) of material samples contained into several sample holders, handle by a robot or any other automatic handling system.

The flowchart presented in FIG. 4E extends the device capabilities by integrating an automatic loading 420 of the sample holder containing the material sample on the measurement station. After the viscoelastic characterization 409 of the material sample, the sample holder is then automatically unloaded 421 from the measurement station for further tests. This protocol is repeated until all the sample holders are analysed.

Figure 4F:
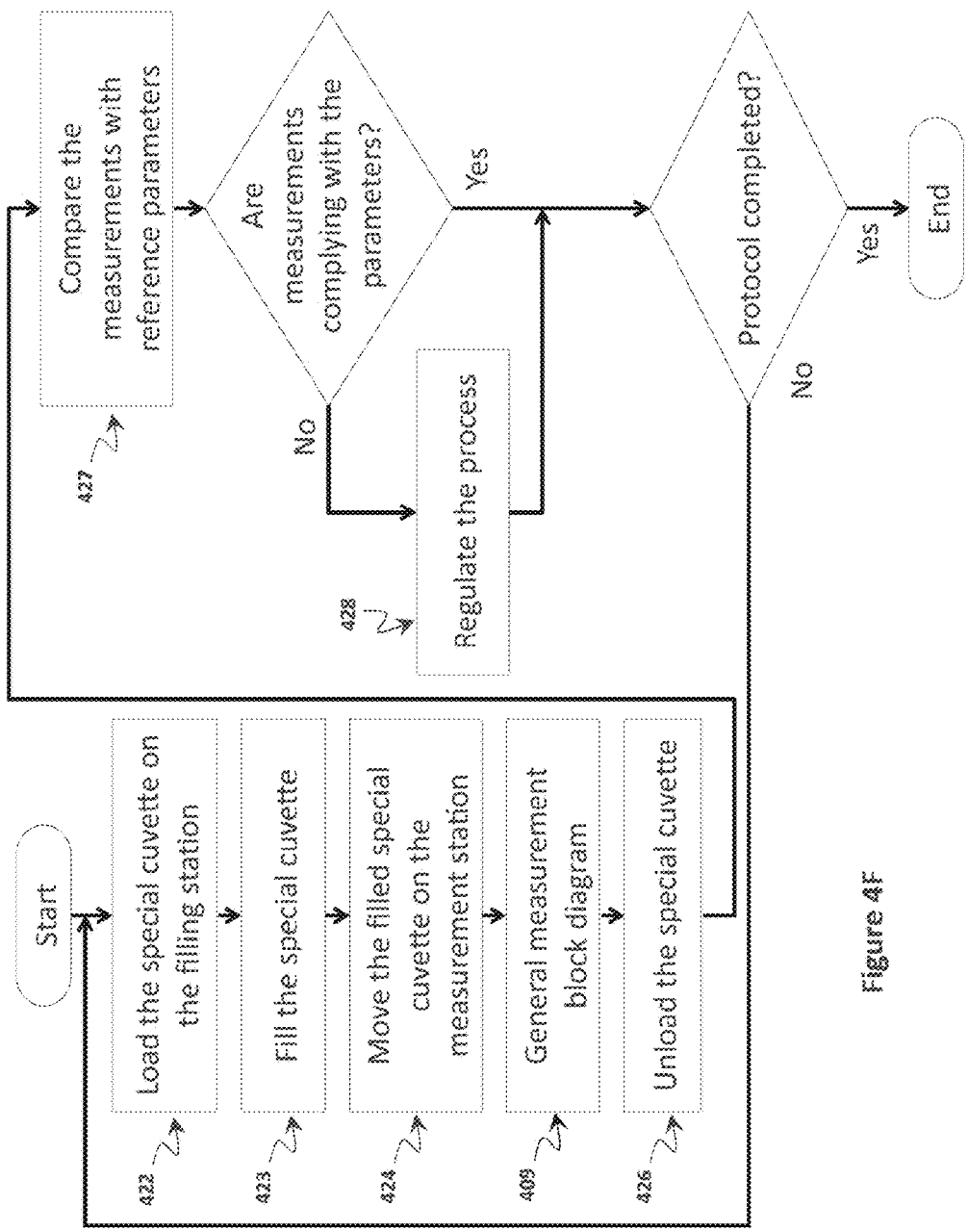
FIG. 4F is a flowchart of mechanical (viscoelasticity) measurements of a material sample automatically poured or positioned into the sample holders using a filling system and for which the sample holder is handled by a robot any other automatic handle system. The mechanical information served as information for real-time process regulation or to perform any other pre-defined known action.

In another aspect of the invention, there is provided a process in which the measurement of viscoelastic properties of materials is part of an industrial process for the manufacturing of products. The various methods and system embodiments described above can be integrated into a manufacturing system to provide measurements in real manufacturing time or quasi real manufacturing time of viscoelastic properties of one or more samples so as to adjust manufacturing parameters or to determine whether a product is ready to move on to the next stage of manufacturing or simply to confirm that the manufacturing is complete or for quality control (to regulate the process). FIG. 4F provides a flow chart summary of a specific example of the integration of the measurements to a production process. The measurements can be performed "in line" with the production process or remotely. The protocol consists in loading 422 the sample holder on the filling station to install or to pour 423 the material sample into the sample holder. This is done by using an automatic feeder like a valve, a tap, an extruder, or any other filling system. The sample holder is then moved 424 automatically or semi-automatically to the measurement station for the viscoelastic characterization 409 of the material sample as function of time to observe transformational kinetics phenomena or for single, punctual measurements. After the measurement, the sample holder is automatically or semi-automatically unloaded 426 from the measurement station and moved to the output zone. In the same time, the viscoelasticity parameters of the material sample are compared 427 with pre-defined and known reference parameters. In the case where the material sample viscoelasticity satisfies the reference parameters, the above-mentioned steps are repeated if the protocol is not completed or stopped if the protocol is completed. If the material sample viscoelasticity is not conformed to the reference parameters (specifications), then the production process is regulated 428 in order to fit the reference parameters. Material samples tested by the device and having non-conform parameters can be selectively rejected from the production or handled separately. The tested materials can also be samples from a production batch. In this case, the conformity or not of the parameters measured by the device can serve to control the environmental and production parameters of the batch. The same information can serve to decide if the quality of the batch is sufficient regarding the production standards. For example, the regulation can consist in modifying the temperature, increase or decrease the humidity, speed up the motor rotation, adapt the flow rate, adjust the quantity of process inputs, display an alarm, any other process parameters useful for the application, or any combination of these parameters operations. The information provided by the device can also serve to accelerate production process, to quantify in real time the quality of products, to determine the best timing or parameters to start a production step.

EXAMPLES

Example 1: Blood Coagulation

The new device can directly measure the absolute viscoelasticity of blood clot samples in terms of shear elastic modulus or Young modulus (in Pascals or other recognized measurement unit) and dynamic viscosity (Pa·s, Pascals seconds). Elastic moduli ranged between about 1 Pa and about 100 mega Pascals and viscosities ranged between 0.001 Pa·s and 20 mega Pa·s can be measured. A sample holder having a soft membrane and a small height compared to its transverse dimensions is connected to the device manually or automatically by a robot. A small and precise volume of liquid blood (between 0.1 mL and 10 mL) is poured in the sample holder. The blood sample can be handled manually or automatically, by a robot, to fill the sample holder using a pipette. The device can contain more than one sample holder in order to perform simultaneous or sequential measurements on several samples. The sample holder is connected to the instrument into a closed environmental chamber that controls the temperature and the humidity of the sample during the test. Temperature can be selected between 0° C. and 100° C. The test duration (from 0.1 seconds to 1200 hours) and the temporal resolution (from 0.1 second to 120 minutes) are selected before starting the test. The measurements are done automatically during the test with respect to the selected parameters: test duration and temporal resolution that determine the number of acquisitions. At each measurement, a gentle vibration is applied to the sample holder in order to produce the vibration of the system composed by the soft membrane and the blood (vibration unit). The vibration of this system is then measured by the device using a non-contact probe and the signal is digitized. The post-processing unit automatically processes the measured signal in order to calculate the spectrum of vibration and to extract the main spectral properties (resonance frequencies, quality factors and amplitude). The post-processing unit calculates, from these spectral characteristics, the current viscoelastic properties (real or complex shear elastic modulus, Young modulus and dynamic viscosity) of the blood sample. The viscoelastic data are then stored and displayed in real time. This process is repeated until the end of the test.

The curves of viscoelasticity evolution over time are used to observe and quantify: clotting time, clotting speed, clotting phases, syneresis time, maximum viscoelasticity of the clot, hemolysis activation time, hemolysis speed, hemolysis phases and viscoelasticity at given characteristic times. These characteristics, and any combination of these characteristics, can then be used to establish a clinical diagnostic, to determine and plan medication posology or to monitor the physiological state of a patient during surgery. The device can be used in hematology laboratories to analyze blood, in point of care to monitor the blood properties of patients over time, in emergency to quickly test blood samples and in surgery rooms to monitor transfusion and control medication. The device can also be used to evaluate, in an in vitro study, the effect of medication molecules (anticoagulant, procoagulant, etc.) on the mechanical properties of the blood during and after the coagulation process in order to develop or improve the medication composition.

Figure 5A:
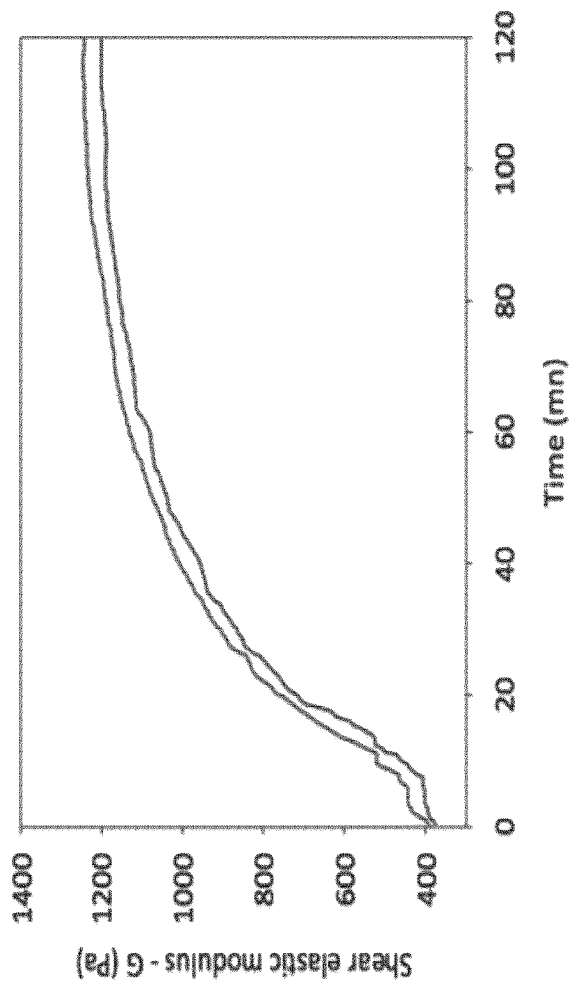
FIG. 5A is a graph of the shear elastic modulus as a function of time of a coagulating blood sample.

FIG. 5A is graph of the shear elastic modulus as a function of time obtained using the method described above and which serves as a means to follow and characterize blood coagulation. In this example pig blood with a hematocrit of 30% was used.

Figure 5B:
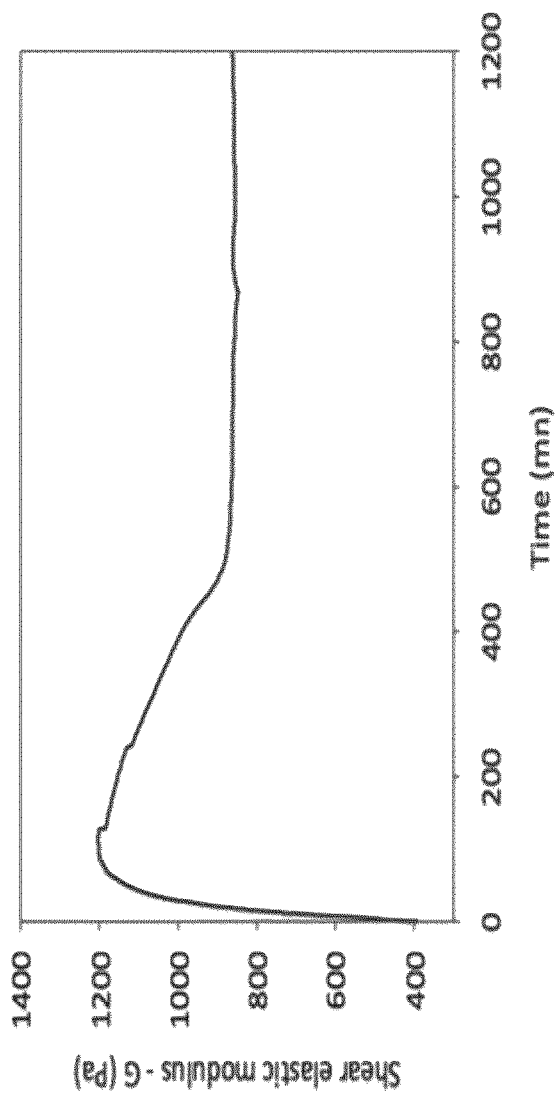
FIG. 5B is a graph of the shear elastic modulus as a function of time of a coagulating blood sample.

FIG. 5B shows a similar graph but recorded over longer period of time in which it is possible to distinguish a reduction of the shear elastic modulus resulting from blood clots dissolution.

The membrane used to make the measurements was made of silicone with a shear storage modulus of 60 kPa. The thickness of the membrane was 1.1 mm and the diameter of the circular sample holder was 10 mm. Numerical parametric simulations have been used to determine the relation between the sample elasticity and the resonance frequency of the system sample/soft membrane (vibration unit).

Example 2

The device allows for the effective measurement of the viscoelastic properties of milk gels during coagulation kinetic. This device measures the gel viscoelasticity in real time with time steps ranged between 0.1 second and 120 minutes and over duration going from 0.1 second to 1200 hours. Since the measurement is done without direct contact with the measurement probe, it is possible to disconnect the sample (with its sample holder) from the device, to store it, and to mount it again in the device to repeat the measurement. Another advantage of the device is its simplicity of use since no expertise is required to run a test. For quality control of products, it is possible to use the device in a completely automated environment in laboratory or at line (i.e. with connection to the production lines or tanks). This allows to control and to optimize the production process based on the mechanical information provided by the device in real time and without human intervention.

Off-Line Uses of the Device

The device can be used in a research and development laboratory to formulate and prototype recipes using the viscoelastic properties of the coagulum and the kinetic of its formation. The device can also serve in research and development in the dairy and food industry to design and prototype production process. The device can be used to control off-line (i.e. out of production lines and tanks) production processes and the quality of final products. For this purpose, samples are taken from the production lines or tanks (at the suitable steps of production) and tested by the instrument in a laboratory environment or in the plant floor. In order to get relevant measurements, the instrument reproduces the same environment as the one of the coagulation tank or production lines (temperature, humidity, food product samples).

For both research and development and quality control applications, the device measures directly the absolute elasticity of coagulated product (for example, milk) in terms of shear elastic modulus or Young modulus (in Pascals or other recognized measurement unit). Elastic moduli ranged between 1 Pa and 100 mega Pascals can be measured. A sample holder having a flexible membrane at the bottom and a small height compared to its transverse dimensions is connected to the device manually or automatically by a robot. A small and precise volume of product (between 0.1 mL and 10 mL) is poured in the sample holder. The product sample can be handled manually or automatically, by a robot, to fill the sample holder using a pipette. The device can contain more than one sample holder in order to perform simultaneous or sequential measurements on several samples. The sample holder is connected to the device into a closed environmental chamber that controls the temperature of the sample during the test. Temperature is selected and controlled between 0° C. and 100° C. The test duration (from 10 seconds to 1200 hours) and the temporal resolution (from 1 second to 120 minutes) can be selected before starting the test. The measurements are done automatically during the duration of the test with respect to the selected parameters: test duration and temporal resolution that determine the number of acquisitions. At each measurement, a gentle vibration is applied to the sample holder in order to produce the vibration of the system composed by the soft membrane and the product (for example, milk). The vibration of this system is then measured by the device using a non-contact probe and the signal is digitized. The post-processing unit automatically processes the measured signal in order to calculate the spectrum of vibration and to extract the main spectral properties (resonance frequencies, quality factors and amplitude). The post-processing unit calculates from these spectral characteristics, the current viscoelastic properties (real or complex shear elastic modulus, Young modulus and dynamic viscosity) of the product sample. The viscoelastic data are then stored and displayed in real time. This process is repeated until the end of the test. At the same time of mechanical testing, many sensors can be also connected to the device to measure in real time various information about the product such as acidity (pH), color, fat, protein or lactose content.

Laboratory testing using the device in the context of research and development contributes to adjust the composition of products and the parameters of a production process. In the case of yogurt, for example, the access to the viscoelastic properties during the coagulation kinetic allows to calculate information like: gelation time, hardening speed, value of elasticity and viscosity at the plateau and other characteristic parameters. Manufacturer can then adapt the recipe and the production process in order to: increase the hardening speed (to improve productivity), control the elasticity and viscosity of the material (to modulate the product texture), minimize the consumption of raw materials (coagulants, texture agents, rheology modifiers), reduce storage time for incubation or firmness improvement (to improve productivity).

At-Line Uses of the Device

The device can serve to perform at-line automatic measurements. In the case of dairy industry, the instrument is coupled to an automatic sampling system connected to the milk fermentation tank or production line. Just before the fermentation starts, the sample holders are automatically filled with milk sampled from the tank or production line. The sample holders can also be automatically mounted in the instrument. The milk in the device is submitted to the same environment as the in the tank (same temperature and humidity). When the fermentation starts in the tank (by stopping the homogenization and by maintaining a constant temperature) or in the incubator, the viscoelastic measurements in the device start. When a given level of elasticity is reached, a signal is sent from the device to the control unit of the production process in order to start another production action or step. For example, in the case of cheese preparation, this action can be the cutting of the curd. In the yogurt industry, it can be the stop of the fermentation process. The information provided by the instrument serves to improve productivity, to avoid unnecessary waiting times, to reduce lost production and to minimize raw materials consumption. The device can also be used at-line (near coagulation tanks) to control production processes of cheese and yogurt. A volume of milk containing enzymes or fermentation activators may be sampled from the tank manually or automatically in order to fill the sample holder. The device measures, as function of time and under controlled conditions, the evolution of the viscoelasticity of the gel. When an optimal elasticity of the milk gel is reached (this elasticity may correspond to maximum yield and target humidity), the device sends a signal to the production automation system in order to start the cutting of the curd.

The device can also be used to monitor a production process. For example, the measured viscoelastic kinetic can serve to monitor fermentation parameters (like temperature profiles) into the fermentation tank or the incubation oven in order to optimize in real time production process. This can significantly contribute to reduce production time, to reduce raw materials consumption (coagulation reagents and texture modifier) and to improve and homogenize quality.

Milk Coagulation

Figure 6A:
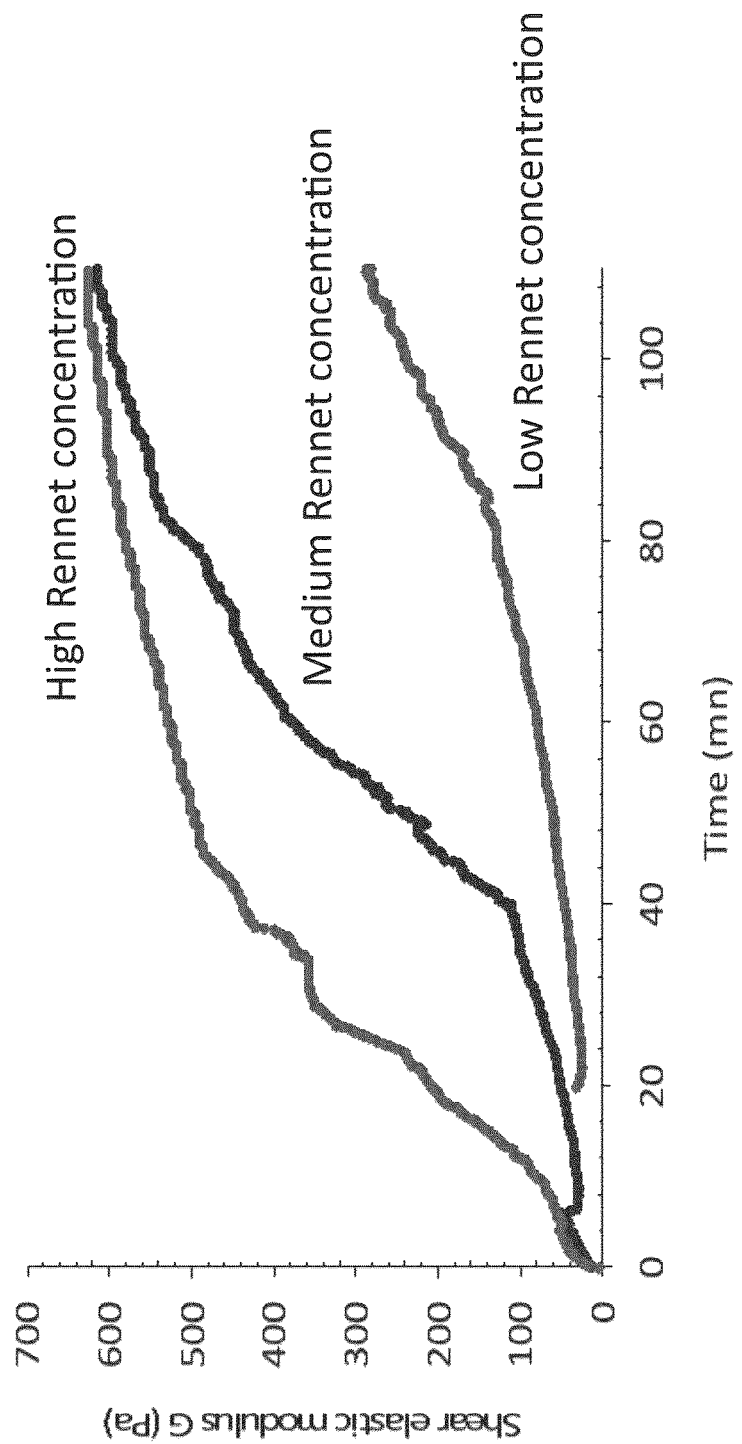
FIG. 6A is a graph of the shear elastic modulus as a function of time of a coagulating milk sample with Rennet solutions at different concentrations.

FIG. 6A is a graph of the shear elastic modulus as a function of time for milk that has been treated with Rennet solutions to induce coagulation. Table 1 provides the study parameters:

TABLE 1

Time evolution of elasticity of milk curd as function of rennet concentration
Test description

| | |
|---|---|
| Milk preparation | Whole pasteurized organic milk with 3.8% fat matter<br>Controlled temperature: 41° C. (±0.5° C.)<br>Sample volume: 1.8 mL |
| Rennet solutions | Rennet: 90% chymosin (Danisco)<br>Rennet solutions: three concentrations<br>Diluted rennet in water:<br>Low concentration = 0.052% v/v (green)<br>Medium concentration = 0.416% v/v (blue)<br>High concentration = 3.328% v/v (red) |
| Temperature | Temperature of 41° C. (±0.5° C.) maintained during the complete duration of the measurements. |
| Time | Time step of 10 seconds between two successive measurements<br>Experiments duration: 100 minutes |

Figure 6B:
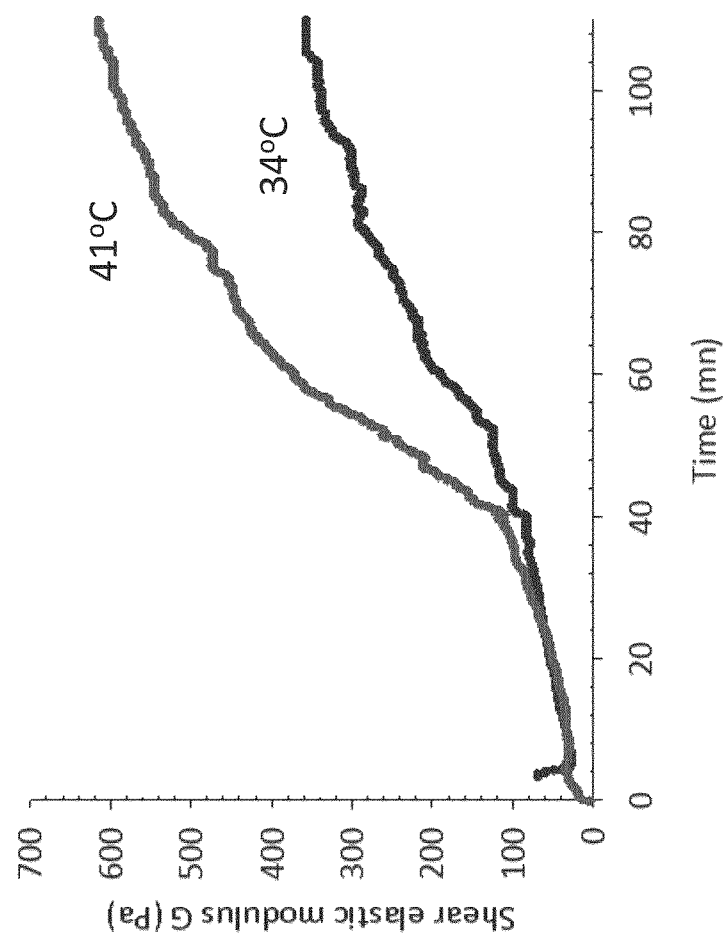
FIG. 6B is a graph of the shear elastic modulus as a function of time of a coagulating milk sample with Rennet solution at different temperatures.

FIG. 6B is a graph of the shear elastic modulus as a function of time for milk that has been treated with Rennet solution at two different temperatures to induce coagulation. Table 2 provides the study parameters.

TABLE 2

Time evolution of elasticity of milk curd as function of temperature
Test description

| | |
|---|---|
| Milk preparation | Whole pasteurized organic milk with 3.8% fat matter<br>Controlled temperature: 41° C. (±0.5° C.)<br>Sample volume: 1.8 mL |
| Rennet solutions | Rennet: 90% chymosin (Danisco)<br>Rennet solutions: three concentrations<br>Diluted rennet in water: 0.416% v/v |
| Temperature | Temperature maintained constant during the tests:<br>Low temperature = 34° C.<br>High temperature = 41° C.<br>Temperature stability = ±0.5° C. |
| Time | Time step of 10 seconds between two successive measurements<br>Experiments duration: 100 minutes |

Example 3

The new device allows measurements the viscoelastic properties of biomaterials and cell cultures in a non-destructive way, without direct contact with the probe and under sterile conditions. The device allows measuring the evolution of viscoelastic properties of biomaterials over time during the gelation process. Samples can be removed from the device to be stored and remounted in the device to be tested again. This allows the mechanical characterization of biomaterials over long periods of time. Biomaterials can be biogels, biogels with cell culture, a cell culture, a biological tissue, or any other biological material.

Elastic moduli ranged between 1 Pa and 1000 mega Pascals can be measured. A sample holder having a flexible bottom and a small height compared to its transverse dimensions is connected to the device manually or automatically by a robot. A small and precise volume of biomaterial (between 0.1 mL and 10 mL) is poured in the sample holder. The biomaterial can contain cells. The biomaterial sample can be handled manually or automatically, by a robot. The device can contain more than one sample holder in order to perform simultaneous or sequential measurements on several samples. The sample holder is connected to the device into a closed environmental chamber that controls the temperature and humidity of the sample during the test. Temperature is selected between 0° C. and 100° C. The test duration (from 10 seconds to 1800 hours) and the temporal resolution (from 1 second to 120 minutes) can be selected before starting the test. The measurements are done automatically during the duration of the test with respect to the selected parameters: test duration and temporal resolution that determine the number of acquisitions. At each measurement, a gentle vibration is applied to the sample holder in order to produce the vibration of the system composed by the soft membrane and the biomaterial. The vibration of this system is then measured by the device using a non-contact probe and the signal is digitized. The post-processing unit automatically processes the measured signal in order to calculate the spectrum of vibration and to extract the main spectral properties like resonance frequencies, quality factors and amplitude. The post-processing unit calculates from these spectral characteristics, the current viscoelastic properties (real or complex shear elastic modulus, Young modulus and dynamic viscosity) of the biomaterial. The viscoelastic data are then stored and displayed in real time. This process is repeated until the end of the test.

The device can serve to formulate biomaterials, to study and control the gelation of biomaterials, to study and control the growth of cells, to measure and modulate the mechanical properties of biomaterials. In terms of quality control of biomaterials in tissue engineering applications, the device can serve as an in vitro routine testing instrument to control the mechanical properties of injectable biomaterials and implanted tissues. The sample holder (containing the biomaterial) can be disconnected from the device to be stored, for example, into an incubator between different measurements. The sample holder can also be connected to a bioreactor to root nutrients to the biomaterial. The sample holder may be sterilized in order to ensure proper conditions for the growth of cells.

Example 4

Formation of Agar Gels

Figure 7:
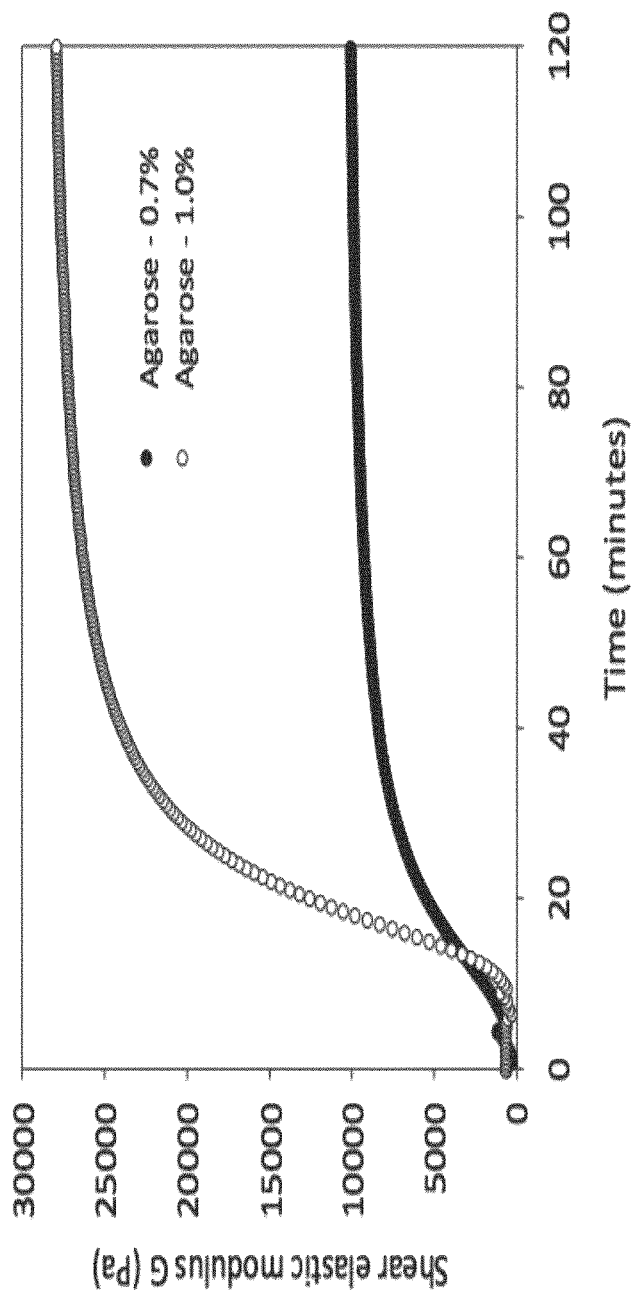
FIG. 7 is a graph of the shear elastic modulus as a function of time of agar gels formation.

FIG. 7 is a graph of the shear elastic modulus as a function of time of agar gel formation. Agar was diluted in water. Two different concentrations were tested (0.7% and 1.0%). The higher concentration sample exhibiting higher shear elastic modulus at longer times.

The sample holders used to measure the viscoelastic properties of coagulating blood and milk, cross-linking silicone and biomaterials presented in this document had a diameter comprised between about 5 mm and 50 mm and a flexural rigidity comprised between about $1 \times 10^{-7}$ and $5 \times 10^{-4}$. In the present examples the dynamic excitation transmitted to the sample holder by the actuator was a transient (single sin cycle) with a central frequency of 700 Hz and a force level ranged between 0.1 N and 50 N. It will be appreciated that the properties of the sample holders and the dynamic excitation may be adjusted as a function of the sample, the detector, type of mechanical property measured and the like.

Example 5

Effect of membrane stiffness and sample shear elastic modulus on the vibration resonance frequency of the vibration unit.

Figure 8:
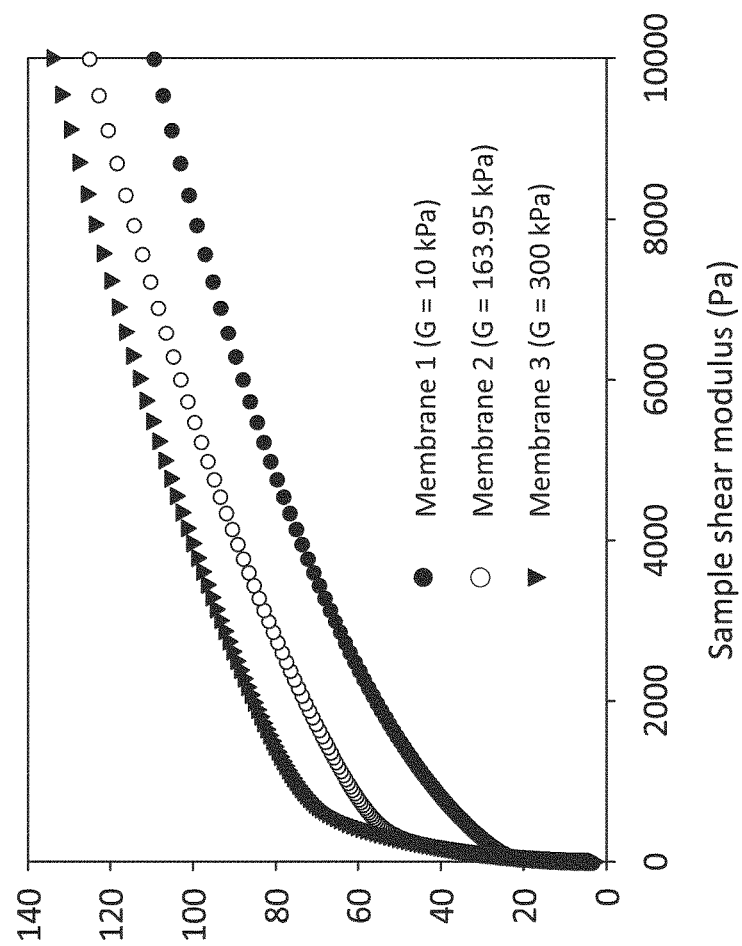
FIG. 8 is a graph of the resonance frequency as a function of the shear elastic moduli of a sample at three different membrane shear elastic moduli.

FIG. 8 is a graph of the vibration resonance frequency as a function of the sample shear elastic modulus. The simulation was tested for three different values of membrane moduli (10 kPa, 163.95 kPa, and 300 kPa). The physical parameters used to run numerical simulations were:
Circular sample holder
Radius of the vibration unit (sample and membrane)=10 mm
Thickness of the sample=6 mm
Thickness of the membrane=1.1 mm
Three simulations were carried out with different membrane shear moduli: 30 kPa, 163.95 kPa and 300 kPa.

The resonance frequency of the vibration unit increases as function of the sample shear modulus. The stiffness of the membrane has an influence on the resonance of the vibration unit. An increase of the membrane stiffness increases the resonance frequency of the system formed by the soft membrane and the sample.

From FIG. 8 it will be appreciated that in a preferred embodiment, the membrane-sample vibration unit exhibits a resonance frequency response as a function of sample stiffness that is a "smooth" function. Preferably, at least part of the response is linear to facilitate the measurements of viscoelastic properties of samples with unknown mechanical properties. The frequency response of each membrane-sample unit is characteristic but it will be appreciated that the responses depicted in FIG. 8, that are representative of the responses that can be obtained with the sample holders and systems described herein, provides an improvement over the prior art in that they allow for sensitive (because of the slope) and reproducibility (because of the "smooth" character of the response). Thus it has been discovered that the combination of the membrane and sample into a vibration unit confers unexpected advantages in terms of the quality of the vibration measurements that can be used to derive the viscoelastic properties of the sample. Furthermore, the system and in particular the sample holder of the invention allows a flexibility of design (by modifying the thickness of the membrane for example) that can be exploited to modify the sensitivity of the response in a simple and effective way.

Example 6

Figure 9:
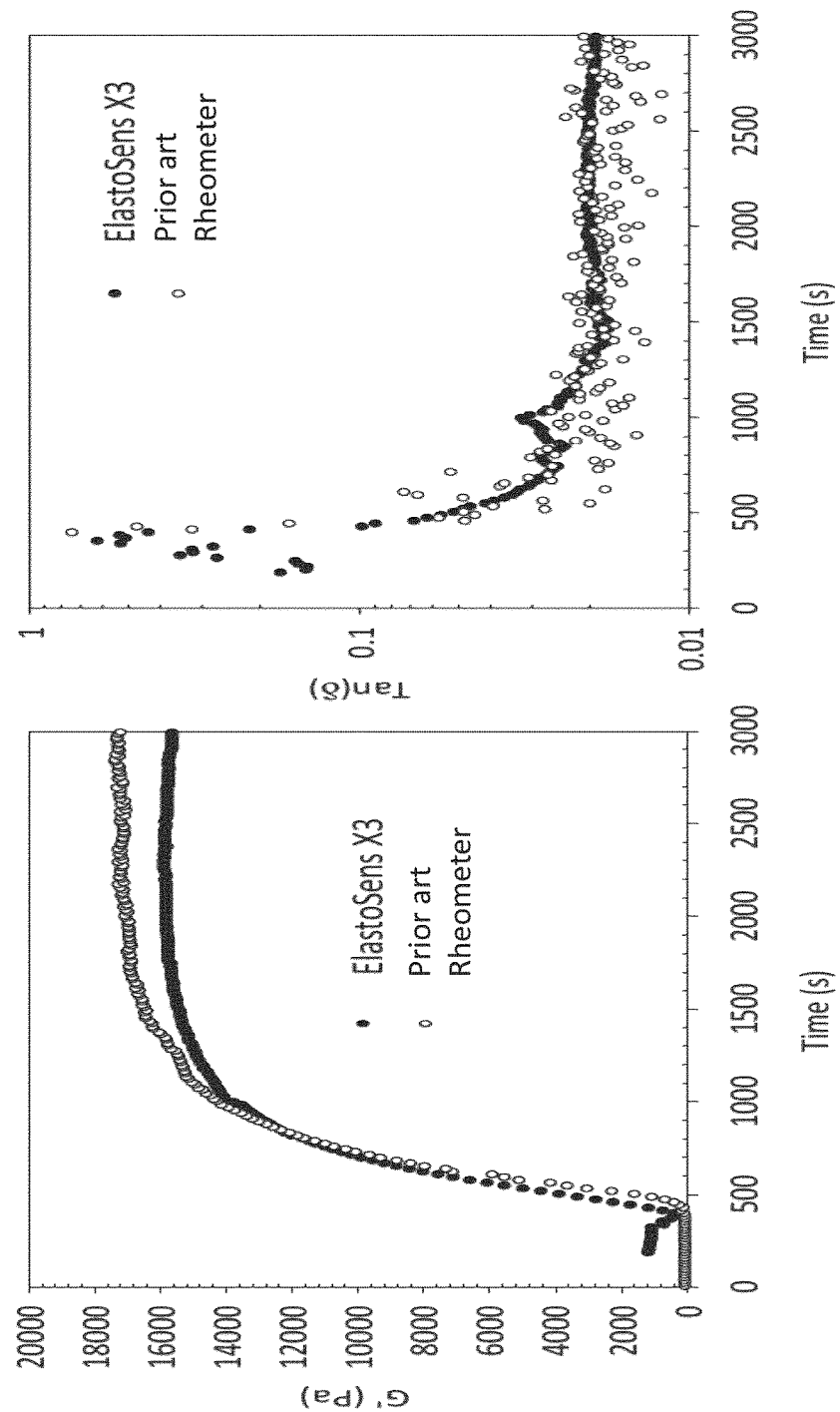
FIG. 9A is a graph of shear elastic storage modulus of agar during cross-linking kinetics (as a function of time) using a system of the invention and a prior art rheometer.
FIG. 9B is a graph of tan(δ) of agar during cross-linking kinetics (as a function of time).

FIG. 9.A and FIG. 9.B show the evolution over time of the shear elastic storage modulus (G') and tan(δ) (tan(δ)=G"/G', with G" the shear elastic loss modulus), respectively, of an agar sample during cross-linking kinetics as measured by a system of the invention and a prior art rheometer.

Figure 10:
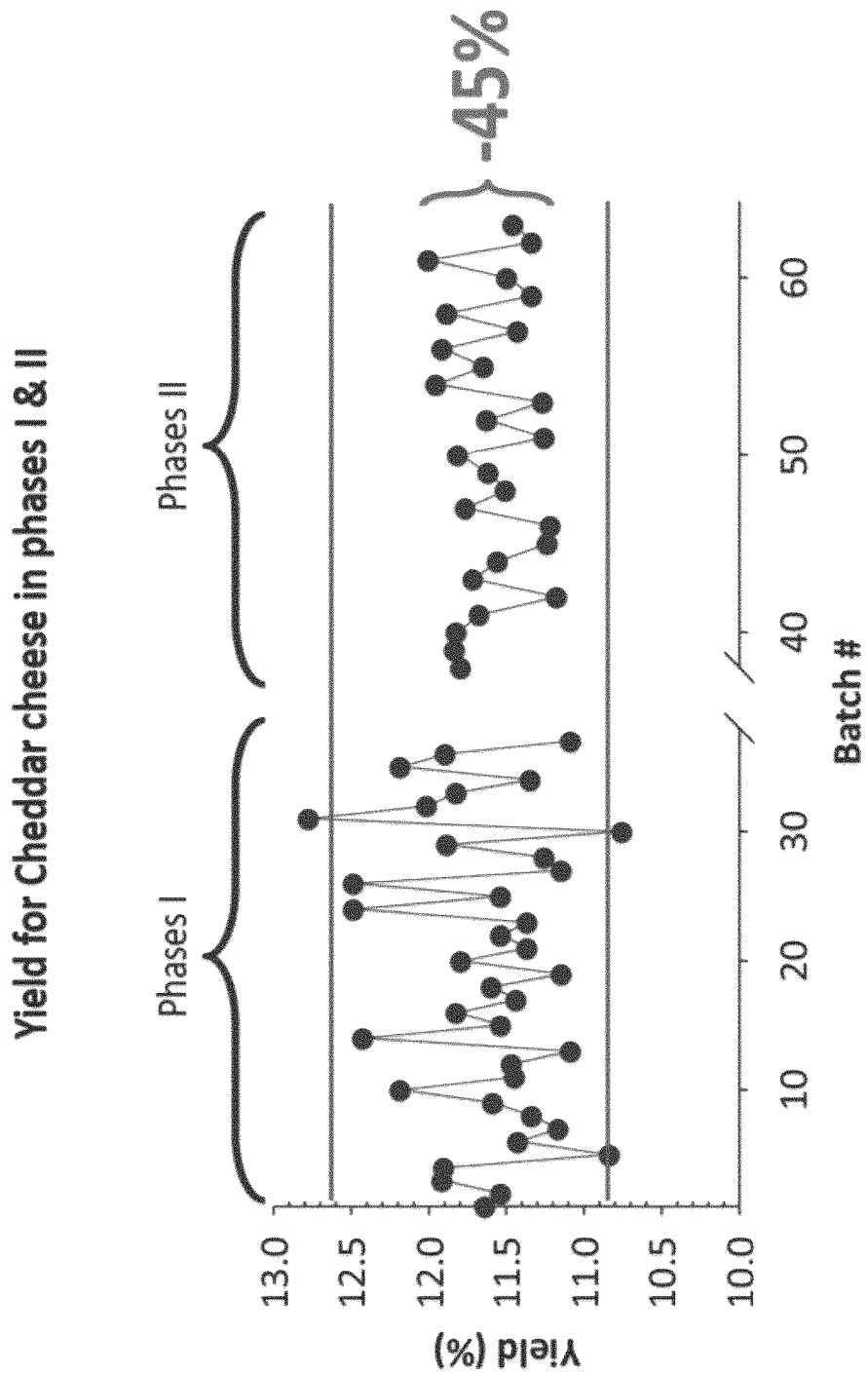
FIG. 10 is a graphic showing the variability in yield of cheddar cheese for process controlled by cheese makers (phase I) or based on viscoelastic properties obtained with a system of the invention (phase II).

FIG. 10 shows the variability of the yield in industrial cheese making process for different production batches without using a system of the invention (ElastoSens X3™) to cut the curd, in phase I, and using a system of the invention to measure the mechanical properties of the curd and proceed to cutting at pre-determined mechanical properties, phase II. One can see that the use of a system of the invention substantially reduces the variability of the yield.

What is claimed is:
1. A sample holder for measuring viscoelastic parameters of a soft sample, the holder comprising:
a main body comprised of material having a flexural rigidity, the main body having a peripheral wall and a bottom to define therewith a closed sample-containing cavity; and
an impermeable membrane having a flexural rigidity lower than the main body flexural rigidity, said membrane extending at least along a portion of the bottom and having an inner face exposed in the sample-containing cavity, such as to retain said soft sample in said holder, and wherein the soft sample is in contact with the membrane to form a vibration unit that is configured to allow vibrations when in the vibrations measurement mode.

2. The sample holder as claimed in claim 1 wherein the membrane has a shear elastic modulus and a flexural rigidity allowing the vibration unit to exhibit resonances when excited to vibrate.

3. The sample holder as claimed in claim 2 wherein the shear elastic modulus of the membrane is from about 1 kPa to about 100 GPa and wherein said flexural rigidity is between about $1 \times 10^-$ and $5 \times 10^{-4}$ Pa*m$^3$.

4. The sample holder as claimed in claim 1 wherein the vibration unit has a known thickness when the soft sample is in the sample holder, and wherein the sample holder is configured to hold liquids.

5. The sample holder as claimed in claim 4 wherein the soft sample has a thickness when in the sample holder and the membrane has a thickness of from about 1/1000 to 1 times the thickness of the soft sample.

6. The sample holder as claimed in claim 4 wherein the sample holder has a length of 1 to 100 times the thickness of the vibration unit.

7. The sample holder as claimed in claim 1 wherein the membrane is selected from elastomers, silicon rubbers and gels.

8. The sample holder as claimed in claim 1 wherein the soft sample is selected from: biological sample, food, polymer, silicone, pharmaceutical product, pharmaceutical excipient, resin, elastomer, gel and plastic.

9. The sample holder as claimed in claim 8 wherein the biological sample is blood or a biomaterial.

10. The sample holder as claimed in claim 9 wherein the sample holder is adapted to allow growth of a biomaterial.

11. The sample holder as claimed in claim 8 wherein the food is milk, cheese, curd, yogurt, or tofu.

12. The sample holder of claim 1 wherein said main body peripheral wall comprises an inner face and wherein said inner face comprises sample displacement stabilizing structures to prevent said sample from slipping during measurements.

13. The sample holder of claim 1 further comprising an attachment configured to secure said holder in a position within a system for measuring viscoelasticity, said position allowing vibration actuation and detection of vibrations of the vibration unit.

14. A system for measuring viscoelasticity of a soft sample comprising:
a sample holder as claimed in claim 1,
a vibration actuator configured to communicate a force to the vibration unit to generate vibrations therein,
a vibration detector configured to acquire measurements of vibrations of the vibration unit, and
a processor for analyzing the measurements of vibrations obtained from the vibration detector to calculate viscoelasticity parameters of the soft sample.

15. The system as claimed in claim 14 wherein the vibration actuator communicates the force by direct contact with a part of the vibration unit.

16. The system as claimed in claim 14 wherein the vibration actuator communicates the force to the vibration unit indirectly by inducing vibration in a member in vibrational contact with the sample holder.

17. The system as claimed in claim 16 wherein the member is a flexible arm and wherein the vibration actuator communicates a bending force to the flexible arm thereby creating a vibration of the arm and sample holder.

18. The system as claimed in claim 14 comprising:
a plurality of sample holders, a sample holder filler to automatically dispense the soft samples in the plurality of sample holders; and
at least one sample holder displacement actuator to provide automated measurement of soft samples contained in sample holders.

19. A method for measuring viscoelastic parameters of a soft sample, the method comprising:
providing a sample in the sample holder as claimed in claim 1,
applying a force to induce vibrations in the vibration unit,
detecting the vibrations from the vibration unit to provide vibration measurements, and
deriving at least one viscoelastic parameter of the soft sample based on the vibration measurements.

20. A process for manufacturing a product comprising:
providing a manufacturing system configured to transform an input material into the product, wherein the transformation comprises one or more stages at which one or more viscoelastic properties of the material are required, and
measuring the viscoelastic properties using the method as claimed in claim 19.

* * * * *